(12) United States Patent
Hayes-Gill et al.

(10) Patent No.: US 8,880,140 B2
(45) Date of Patent: Nov. 4, 2014

(54) ELECTRODE AND ELECTRODE POSITIONING ARRANGEMENT FOR ABDOMINAL FETAL ELECTROCARDIOGRAM DETECTION

(75) Inventors: Barrie Robert Hayes-Gill, Nottingham (GB); Carl William Barratt, Nottingham (GB); Jean-Francois Pieri, Nottingham (GB)

(73) Assignee: Minoca Healthcare Limited, Nottingham (GB)

( * ) Notice: Subject to any disclaimer, the term of this patent is extended or adjusted under 35 U.S.C. 154(b) by 339 days.

(21) Appl. No.: 12/997,566

(22) PCT Filed: Jun. 12, 2009

(86) PCT No.: PCT/GB2009/001507
§ 371 (c)(1),
(2), (4) Date: Mar. 7, 2011

(87) PCT Pub. No.: WO2009/150440
PCT Pub. Date: Dec. 17, 2009

(65) Prior Publication Data
US 2011/0306862 A1    Dec. 15, 2011

(30) Foreign Application Priority Data

Jun. 13, 2008 (GB) .................................. 0810843.3
Oct. 30, 2008 (GB) .................................. 0819887.1

(51) Int. Cl.
*A61B 5/0448* (2006.01)
*A61B 5/0408* (2006.01)
*A61B 5/00* (2006.01)

(52) U.S. Cl.
CPC ........... *A61B 5/0448* (2013.01); *A61B 5/04085* (2013.01); *A61B 5/04087* (2013.01); *A61B 5/4362* (2013.01)
USPC ............ 600/382; 600/511; 600/391; 600/393

(58) Field of Classification Search
CPC .. A61B 5/0011; A61B 5/0444; A61B 5/0448; A61B 5/04485; A61B 5/04882; A61B 5/4362; A61B 5/4356; A61B 5/6823; A61B 5/8631; A61B 5/6832; A61B 5/684; A61B 2560/04; A61B 2560/0412; A61B 2560/0468; A61B 2562/04; A61B 2562/164

USPC .......... 600/382, 509, 511, 588, 376, 386–393
See application file for complete search history.

(56) References Cited

U.S. PATENT DOCUMENTS

| | | |
|---|---|---|
| 3,998,215 A | 12/1976 | Anderson et al. |
| 4,706,680 A | 11/1987 | Keusch et al. |

(Continued)

FOREIGN PATENT DOCUMENTS

| | | |
|---|---|---|
| EP | 0263586 A2 | 4/1988 |
| EP | 0269200 A1 | 6/1988 |

(Continued)

OTHER PUBLICATIONS

Ambu, Inc. "Neuroline 710" and "Neuroline 720" electrode datasheets (Jan. 2008) retrieved from Ambu.com website via Wayback Machine.*

(Continued)

*Primary Examiner* — Lee S Cohen
*Assistant Examiner* — Erin M Cardinal
(74) *Attorney, Agent, or Firm* — Perkins IP Law Group LLC; Jefferson Perkins

(57) ABSTRACT

The invention relates to large area electrodes suitable for use in a fetal heart rate monitoring systems. The electrode comprises: a cutaneous gel contact (10) for sensing fetal electrocardiogram signals from a human pregnant subject; an electrical conductor (12) electrically connected to the gel contact (10) so as to define a first electrical contact region; a connector (14) in electrical contact with the electrical conductor (12) for connection to a lead wire; and a substructure (16) for attachment to a human pregnant subject. The gel contact (10) and the electrical conductor (12) are arranged on the substructure (16) to allow a contact surface (11) of the gel contact (10) to be in electrical communication with the skin of a human pregnant subject to define a second electrical contact region. The second electrical contact region has an area greater than 370 square millimeters. When arranged on a predefined electrode topology on the abdomen the success rate of fetal heart rate detection is significantly improved. The topology may be incorporated into a flat flexible cable which provides a comfortable and reproducible electrode arrangement allowing an untrained person to apply electrodes to a pregnant mother's abdomen.

25 Claims, 17 Drawing Sheets

(56) References Cited

U.S. PATENT DOCUMENTS

| | | | |
|---|---|---|---|
| 4,848,353 A | 7/1989 | Engel | |
| 5,133,356 A | 7/1992 | Bryan et al. | |
| 5,197,472 A | 3/1993 | DiSabito | |
| 5,362,420 A | 11/1994 | Itoh et al. | |
| 5,807,271 A * | 9/1998 | Tayebi et al. | 600/511 |
| 6,751,498 B1 | 6/2004 | Greenberg et al. | |
| 7,532,923 B1 * | 5/2009 | Hayes-Gill et al. | 600/511 |
| 8,483,810 B2 * | 7/2013 | Lee et al. | 600/511 |
| 2001/0051821 A1 | 12/2001 | Snyder | |
| 2004/0243015 A1 * | 12/2004 | Smith et al. | 600/511 |
| 2005/0122883 A1 | 6/2005 | Kimura | |
| 2005/0267376 A1 | 12/2005 | Marossero et al. | |
| 2005/0267377 A1 | 12/2005 | Marossero et al. | |
| 2005/0277841 A1 | 12/2005 | Shennib | |
| 2006/0189882 A1 * | 8/2006 | Thomas | 600/546 |
| 2007/0213627 A1 * | 9/2007 | James et al. | 600/511 |
| 2007/0260133 A1 | 11/2007 | Meyer | |
| 2011/0092837 A1 * | 4/2011 | Lee et al. | 600/511 |

FOREIGN PATENT DOCUMENTS

| | | |
|---|---|---|
| EP | 1700564 A2 | 9/2006 |
| EP | 1854403 A2 | 11/2007 |
| WO | 2001026545 A1 | 4/2001 |
| WO | WO 0126545 A1 * | 4/2001 |
| WO | 2003028550 A2 | 4/2003 |
| WO | 2005122883 A2 | 12/2005 |
| WO | 2007085068 A1 | 8/2007 |
| WO | WO 2009013246 A1 * | 1/2009 ............ A61B 5/0444 |

OTHER PUBLICATIONS

The International Bureau of WIPO, International Preliminary Report on Patentability, issued Dec. 14, 2010 in connection with International Patent Application No. PCT/GB2009/001507.

Van Oosterom, A. et al., "Lead systems for the abdominal fetal electrocardiogram", Clinical Physics and Physiological Measurement, 1989, p. 21-26, vol. 10, Supplement B, Institute of Physics Publishing, Bristol, GB.

UK Intellectual Property Office, Search Report on Application No. GB0810843.3 (Claims 1-15 only searched), dated Oct. 10, 2008.

UK Intellectual Property Office, Search Report on Application No. GB0810843.3 (Claims 16-44 searched), dated Jan. 6, 2009.

Conmed Catalogue 2004, "Resting EKG electrodes", downloaded from http://www.conmed.com/PDF%20files/MBR%209047%20Restine%20EKG.pdf on Oct. 10, 2008.

3M Catalog 2007/2008, "Red Dot Biomedical electrodes", downloaded from http://multimedia.3m.com/mws/mediawebserver?66666UuZjcFSLXTtIXfEMXTEEVuQEcuZgVs6EVs6E666666— on Oct. 10, 2008.

Huigen, E. et al., "Investigation into the origin of the noise of surface electrodes," Medical and Biological Engineering & Computing, 2002, p. 332-338. vol. 40.

Puurtinen, Merja M. et al., "Measurement of noise and impedance of dry and wet textile electrodes, and textile electrodes with hydrogel," Proceedings of the 28th IEEE, EMBS Annual International Conference, New York City, USA, Aug. 30-Sep. 3, 2006.

Rai et al., "Symphysis fundal height curve—a simple method for foetal growth assessment," Journal of PG Medicine, 1995, vol. 41, Issue 4, pp. 93-94.

European Patent Office, Examination Report for European Patent Application No. 09 761 989.4-1660 issued on Nov. 19, 2013.

Potter Clarkson, Response to Examination Report on European Patent Application No. 09 761 989.4-1660 (issued on Nov. 19, 2013), dated Jan. 7, 2014.

State Intellectual Property Office of the People'S Republic of China, Third Office Action on Patent Application No. 200980131538.3 issued on Nov. 12, 2013.

* cited by examiner

ELECTRODE AND ELECTRODE POSITIONING ARRANGEMENT FOR ABDOMINAL FETAL ELECTROCARDIOGRAM DETECTION

The invention relates to the optimisation of electrodes and electrode positioning arrangements for the detection of abdominal fetal electrocardiogram (fECG) signals.

In order to detect the abdominal fECG signal, electrical contact needs to be established between an fECG monitoring device and the maternal abdomen.

In the prior art, electrical contact has been established through a wet gel (which can be either in a "liquid" or "solid" form) ECG electrode designed for detecting adult ECG signals. Two such adult ECG wet gel electrodes are the 3M 2271 (solid wet gel) and the Ambu VLC-00-S (liquid wet gel). The 3M 2271 has a circular electrode contact region of diameter 18 millimeters and an area of approximately 255 square millimeters. The Ambu VLC-00S also has a circular electrode contact region but with a diameter of 19 millimeters and an area of approximately 284 square millimeters.

As used herein the term "electrode contact region" encompasses the contact area between the skin of a subject and the sensing element of an electrode i.e. the surface area through which current flow can pass between the skin and the electrode. In the case of wet gel electrodes "electrode contact region" refers to the surface of the gel in contact with the subject's skin.

The term "wet gel" is used throughout this document to refer to both a "liquid wet gel" and a "solid wet gel". A solid wet gel comprises a gel with a relatively high viscosity when compared to a liquid wet gel. Both solid and liquid wet gels exude liquid when compressed. A hydrogel is tacky to the touch but does not exude any liquid when compressed.

Alternatively, other varieties of electrode such as hydrogel electrodes, dry electrodes and non contact electrodes may be used to detect ECG signals. A hydrogel electrode may be made from either natural karaya gum or synthetic polyvinyl pyrrolidone.

The magnitude of the fECG signal is typically between 0.1 and 40 microvolts. This represents a significantly reduced signal strength when compared to e.g. the adult ECG signal which is typically 1000 to 5000 microvolts.

The reduction of noise on the detected fECG signal is therefore of great importance. This noise on a detected fECG signal varies considerably and is typically caused by one or more of the following:

Amplifier voltage noise (both white and flicker)—$V_{Vrms}$
Amplifier Current Noise (both white and flicker)—$V_{irms}$
Electrode Noise (both white and flicker)—$V_{Erms}$
Muscle Noise (Electromyogram)—$V_{mrms}$
Ambient electromagnetic pick-up noise—$V_{EMIrms}$
Cable triboelectric/EMI noise—$V_{Crms}$ The total noise is calculated as the square root of the sum of the squares of all of these noise components i.e.

$$\text{Vn\_total} = \sqrt{V_{Vrms}^2 + V_{irms}^2 + V_{mrms}^2 + V_{Erms}^2 + V_{EMIrms}^2 + V_{Crms}^2} \quad \text{Equation 1}$$

Hence if one noise source dominates by say 4 times over the others then the contribution of each of the smaller components is only ~5% of the total. Over the years there has been continual reduction in the amplifier noise performance such that these components can be neglected as long as the source impedance is kept below approximately 3,000 ohms. An aspect of the invention relates to the overall reduction in the remaining noise components.

A key factor in the noise reduction is the skin impedance at the site of the electrode. The larger the skin impedance the greater the electrode noise. Where skin impedance is held constant by suitable skin preparation, wet gel electrodes exhibit the most favourable noise characteristics, which has resulted in wet gel electrodes of the type already mentioned being the electrode of choice in abdominal fECG detection. This is assumed to be due to both the reduction in 1/frequency (flicker) noise and increased ion transport with the wet gel electrodes compared to the hydrogel electrodes.

Existing techniques for the reduction in skin impedance at the site of fECG electrodes include the preparation of the skin surface prior to electrode application. Exfoliation creams and abrasive papers are used to remove dead skin cells on the epidermal layer.

The use of abrasive techniques to reduce skin impedance can lead to irritation of the skin and reduced subject compliance if prolonged or frequent monitoring of the fECG is required.

A further consideration when seeking to minimise noise on an fECG signal is the area of the contact region of the electrode. The noise of an electrode is related to the area of the electrode contact region by:

$$N \alpha 1/\sqrt{A} \quad \text{Equation 2}$$

where N is the voltage noise and A is the area of the electrode contact region. A larger electrode contact region is therefore desirable in order that noise on an fECG signal is minimised.

However, the selection of an electrode with a particular contact area also depends on the required spatial sensitivity and the type of electrophysiological application.

For example the detection of EEG from the brain requires small electrodes typically with a contact area of 6 to 9 millimeters in diameter. This small area contact region is required in order to detect the individual electroencephalogram signals from different regions of the brain. Were a larger electrode deployed in this application then the individual signals from the brain would be averaged across the electrode contact area.

As mentioned above, adult ECG wet gel electrodes are typically 18 or 19 millimeters in diameter or may even be as large as 21 millimeters in diameter. These electrodes are employed in adult vector-cardiography whereby different regions of the adult chest exhibit specific electrical signals indicative of cardiac function. Again, use of larger electrodes may result in the averaging of two intercostal electrode positions and a loss of spatial sensitivity. The area of the contact region in adult vector-cardiography ECG wet gel electrodes has therefore been limited to maintain spatial sensitivity.

Use of the adult ECG wet gel electrode in detection of the fECG has led to an increased need for abrasive preparation of maternal abdominal skin and to large levels of noise being present on the detected fECG signal.

An increase in electrode contact region would lead to an improved signal-to-electrode noise ratio (referred to as signal-to-noise ratio hereinafter) of an electrode allowing easier detection of an fECG signal and/or a reduction in skin preparation requirements.

However, the fECG signal is not evenly distributed across the maternal abdomen. The relationship between the increased electrode contact region and the improvement in signal-to-noise ratio is therefore not linear. If the electrode contact region of an electrode were to cover areas of the maternal abdomen where the fECG signal is weak or not present, the averaging effect of the electrode would result in a weakening of the detected fECG signal and a reduction in signal-to-noise ratio.

Optimization of the size of electrode contact region, and of the placement of each electrode has a large effect on the signal-to-noise ratio of the fECG signal.

Another aspect of fECG detection is the relative geometry of each of the fECG electrodes. fECG monitors such as the Monica Healthcare AN24 use three channels to increase the probability of detection of the fECG signal. The electrodes are typically placed in the configuration depicted in FIG. 1.

Electrodes 1, 2 and 3 are positioned on the maternal abdomen approximating an arc which is substantially the same as the arc of the subject's uterus fundus. Electrode 4 is placed at a location approximating the symphis pubis of the subject. Electrode 4 may be placed between 2 cm and 5 cm above the symphis pubis. The positioning of the electrodes 1 to 4 is important to the quality of the fECG signal detected.

A fifth electrode (not shown) is optionally attached to the back or side of the subject for use as a right leg driver electrode.

The term "right leg driver electrode" when used throughout this document relates to an electrode placed on the body of the subject to drive a signal back into the subject to cancel out signals common to each of the electrodes 1, 2 and 3 and their connecting wires. Removing these common mode signals from the signal detected by electrodes 1, 2 and 3 improves the fECG signal quality and therefore the probability that the fECG can be extracted.

The leads 6 which connect the electrodes 1, 2, 3, 4 to the fECG monitor (not shown) are inconvenient, unsightly and may cause discomfort to the subject during monitoring.

According to one aspect, the invention provides a large area wet gel electrode that has a greatly increased electrode contact region. The increase in electrode contact region reduces the noise on the detected fECG signal and allows for a reduction in the amount of abrasive skin preparation required prior to fECG monitoring.

According to another aspect the invention provides a multi-electrode patch upon which electrodes are positioned to ensure their optimal relative placement for detecting fECG signals. Leads are contained within the patch, which forms a flexible flat cable, to ensure that they are neatly contained and will cause minimum discomfort to the subject. Incorporating the leads and electrodes into a flat flexible cable provides a comfortable and reproducible electrode arrangement allowing an untrained person (or the patient themselves) to apply the multi-electrode patch to a pregnant mother's abdomen.

According to another aspect of the invention there is provided an electrode suitable for use in a fetal heart rate monitoring system. The electrode comprises: a cutaneous contact for sensing fetal electrocardiogram signals from a human pregnant subject; an electrical conductor electrically connected to the contact so as to define a first electrical contact region; a connector in electrical contact with the electrical conductor for connection to a lead wire; and a substructure for attachment to a human pregnant subject. The contact and the electrical conductor are arranged on the substructure to allow a surface of the contact to be in electrical communication with the skin of a human pregnant subject to define a second electrical contact region, wherein the second electrical contact region has an area greater than 370 square millimeters.

The term "cutaneous contact" encompasses an electrical contact which is, in use, in contact with the skin of a pregnant subject and capable of detecting electrical signals present in the body. It may be e.g. a wet gel electrode or a hydrogel electrode.

The increased area of the second electrical contact area allows for the reduction of noise on the detected fECG signal. This can reduce the need for preparation of the subject's skin before attachment of the electrode. The reduction in required skin preparation leads to greater subject comfort and compliance.

The previous use of adult ECG electrodes in the detection of fECG signals from the maternal abdomen has prejudiced the prior art toward a smaller electrode than is necessary. As has been discussed above, the electrode contact region of adult vectorcardiography ECG electrodes has been limited by the need to maintain spatial sensitivity. However, in certain applications relating to the detection of fECG, such as the monitoring of fetal heart rate, spatial sensitivity is of lesser importance and larger area electrodes can be used.

A second electrical contact area of 370 square millimeters provides an improvement over adult ECG wet gel electrodes of approximately 15% in signal-to-noise ratio or a reduction in skin preparation assuming a constant gel resistivity and depth. This is shown in greater detail below.

In one embodiment the electrode may be a wet gel electrode and the contact may be a gel contact.

In another embodiment the second electrical contact region may be greater than 490 square millimeters. A second electrical contact area of 490 square millimeters increases the effect of the benefits stated above.

In another embodiment the first electrical contact area may be greater than 300 square millimeters. In another embodiment the first electrical contact area may be greater than 415 square millimeters. The large area of the first electrical contact area further improves the gel-to-conductor impedance further leading to reduced noise characteristics of the electrode.

In certain embodiments of the invention the first and second contact region may have a substantially rectangular, elongated or crescent shape or a circular shape. The rectangular, elongated or crescent shape of the electrode reduces any parasitic electromyogram (EMG) signal produced by the muscles of a subject. An elongated electrode running transverse to, and preferably at right angles to, the abdominal muscle results in a reduced spatially averaged EMG signal. This can reduce noise on the detected fECG signal caused by EMG signals.

In preferred embodiments the resistivity of the gel contact may be between 1 and 20 ohm centimeters. In other preferred embodiments the resistivity of the gel contact may be between 20 and 100 ohm centimeters.

The resistivity of the saline gel used in the gel contact has a direct impact on the resistance of the gel contact itself and the noise associated with the electrode. Resistance R is given by:

$$R = \rho l / A \qquad \text{Equation 3}$$

where $\rho$ is the resistivity of the gel contact, l is the depth of the gel contact and A is the sectional area of the gel contact.

The electrical conductor may be a metal film. Particularly, the electrical conductor may be a silver/silver chloride film. The use of a metal or, more particularly, a silver/silver chloride film for the electrical conductor reduces the impedance of the gel-to-conductor electrical contact area due to the low resistivity of the metal. Silver is preferred since it has a reduced polarisation with the saline gel. The use of silver chloride is so as to provide an electrically stable metallic surface (i.e. with low inherent noise) whilst the silver is in contact with the saline gel.

The gel contact may include a saline gel solution, the saline gel solution being held within a sponge and the sponge being secured on the substructure to permit electrical communication between the saline gel and the electrical conductor. The viscosity of the saline gel is often increased such that the sponge and gel together form what is called a "solid wet gel".

In a preferred embodiment the substructure includes an adhesive capable of adherence to the skin of a pregnant subject. The adhesive allows the electrode to be fixed at the required location site on the abdomen of a pregnant subject.

According to another aspect of the invention there is provided a multi-electrode patch for use with a fetal heart rate monitor. The multi-electrode patch comprises: a flexible substructure attachable to the skin of a pregnant subject; at least three sensing electrodes positioned on the flexible substructure to approximate an arc, wherein the arc approximated by the at least three sensing electrodes is substantially the same in length and radius as the arc formed by the uterus fundus of a human pregnant subject; and at least one connection port electrically connected to each sensing electrode and permitting electrical connection to a fetal heart rate monitor.

The multi-electrode patch ensures that each of the at least three electrodes arranged on the patch are in their optimal relative positions with regard to the detection of fECG signals from a maternal abdomen.

Electrode placement without the multi-electrode patch of the invention is open to some amount of interpretation by the user. This may adversely affect the quality of the detected fECG signal. Placing electrodes using the multi-electrode patch substantially increases the likelihood that each electrode is optimally located on the maternal abdomen relative to the other electrodes on the patch. Incorporating the leads and electrodes into a flat flexible cable provides a comfortable and reproducible electrode arrangement allowing an untrained person (or the patient themselves) to apply the multi-electrode patch to a pregnant mother's abdomen.

In one embodiment the multi-electrode patch may further include a common electrode, wherein the common electrode is electrically connected to the at least one connection port and is arranged on the flexible substructure, such that in use the distance between the at least three sensing electrodes and the common electrode is substantially the same as the distance between the uterus fundus and the symphis pubis of a pregnant subject.

The common electrode provides a common reference for signals detected by each of the at least three electrodes and its position relative to the at least three electrodes can therefore have an impact on detected fECG signal quality. The inclusion of this electrode on the multi-electrode patch therefore removes the need for the user to correctly interpret the optimal common electrode position.

In another embodiment the common electrode may be located on an umbilical type patch. The umbilical type patch may be connected to the multi-electrode patch such that the common electrode may be placed at or near the symphis pubis, or on the back, of the pregnant subject. When used on the back the common electrode is positioned above the coccyx but below the 10$^{th}$ thoracic vertebra.

The multi-electrode patch may also include a right leg driver electrode, wherein the flexible substructure includes a spur portion, the right leg driver electrode being located at the distal end of the spur portion. It is not essential for the right leg driver electrode to use a large area electrode since it is not a sensing electrode but a driving electrode.

The at least three electrodes of the multi-electrode patch may preferably include wet gel electrodes. The wet gel electrodes may include electrodes which define an electrode contact region greater than 370 square millimeters. In another embodiment the at least three electrodes may include electrodes which define an electrode contact region greater than 490 square millimeters.

The large electrode contact region of each electrode reduces the noise on the detected fECG signal. The large electrode contact region also permits reduced skin preparation prior to attachment of the multi-electrode patch.

The multi-electrode patch may advantageously include electrodes which define a substantially rectangular, elongate or crescent electrode contact region. As previously discussed this allows for the reduction of parasitic EMG signals in the detected fECG signal.

Preferably the at least three sensing electrodes are equispaced along the length of the arc. This configuration provides the best chance of detection of the fECG signal when the multi-electrode patch is applied to the maternal abdomen.

The spacing of the at least three sensing electrodes along the length of the arc may be: between 80 mm and 100 mm; between 130 mm and 150 mm; 155 mm and 175 mm; or 230 mm and 250 mm.

The various spacing options for the sensing electrode allow the production of multi-electrode patch of varying sizes, dependent on the gestation time of the pregnant subject. Such varying sizes also accommodate varying body mass indices (BMI).

The multi-electrode patch may include at least one additional sensing electrode positioned on the line of the arc defined by the at least three sensing electrodes and spaced from a central electrode of the at least three sensing electrodes at a distance different to the spacing of the at least three sensing electrodes. The at least one additional electrode may be spaced from a central electrode of the at least three sensing electrodes by one or more of between 80 mm and 100 mm, between 130 mm and 150 mm, between 155 mm and 175 mm and between 230 mm and 250 mm.

Supplying a multi-electrode patch having additional sensing electrodes spaced differently than the at least three sensing electrodes allows the production of a patch that can be used on pregnant subjects of different gestation times.

The various sensing electrodes on the patch may be positioned to correspond to favourable positions on the pregnant subject's abdomen for sensing fECG signals at different gestation times. The operator of the fECG monitoring device can connect the device to the sensors that provide the best chance of detected the fECG signal.

The at least three sensing electrodes may advantageously be electrically connected to the connection port by shielded wiring. In a particular embodiment of the invention the flexible substructure and shielded wiring form a flexible flat cable.

The shielded wiring provides resistance to interference from external signals and reduces the noise on the fECG signal introduced through the wiring. The voltage potential of this shield is the common mode voltage of electrodes 1, 2 and 3. An antiphase signal is then generated from this common mode signal and is presented at the output of the right leg driver.

Additionally, the incorporation of the wiring and the flexible substructure to form a flexible flat cable constrains the wiring preventing it from appearing unsightly and interfering with the process of fECG monitoring. The flat flexible cable when laid against the pregnant mother's abdomen also reduces unwanted inductive pick-up loops.

Preferably the flexible substructure includes an adhesive capable of adherence to the skin of a pregnant subject.

According to another aspect of the invention there is provided a method for taking fetal ECG measurements. The method comprises the steps of: a) providing a multi-electrode patch as previously defined; b) establishing a first line on the skin of a pregnant subject to approximate the line of the uterus fundus; c) placing the multi-electrode patch on the skin of the pregnant subject such that the at least three sensing electrodes are positioned along a line approximating the first line; d) placing a common electrode on the skin of the pregnant subject at a location opposing the location of the at least three sensing electrodes such that a line taken between the common electrode and each of the sensing electrodes passes through the womb of the pregnant subject; and e) taking an fECG measurement using any combination of the said at least three sensing electrodes referenced against the common electrode.

The method of correct placement of the multi-electrode patch provides electrodes which are optimally relatively positioned on the abdomen of the pregnant subject for the detection of fECG signals.

Placing the common electrode at a location opposing the location of the three sensing electrodes encompasses placing the common electrode such that the electrode contact region of the common electrode substantially faces the electrode contact region of the sensing electrodes. A vector drawn between the common electrode and each of the sensing electrodes should pass through the womb of the pregnant subject.

In one embodiment the method may include, at step d), placing the common electrode at a location approximating the symphis pubis of the pregnant subject. Electrode 4 may be placed between 2 cm and 5 cm above the symphis pubis.

In another embodiment the method may include, at step d), placing the common electrode on the back of the pregnant subject.

The method may include the sub-step of: d) i) placing a right leg driver electrode on the back or abdominal side of a pregnant subject. As previously explained this additional sub-step allows the removal of common mode signals common to all electrodes and connecting cables from the fECG signal.

Step c) of the method may include establishing a second line on a pregnant subject, the second line being parallel to the first line and passing through the Xiphoid Process of the subject and placing the multi-electrode patch on the skin of a pregnant subject such that the at least three electrodes are positioned between the first line and the second line.

Additionally, step c) of the method may further include establishing a third line on a pregnant subject, the third line being parallel to the first line and located up to 100 mm away from the first line, and placing the multi-electrode patch on the skin of a pregnant subject such that the at least three electrodes are positioned between the third line and the second line.

Experience of over 800 recordings has shown that the fECG amplitude can vary in a complex manner across the abdomen from patient to patient. It has been found that the best fECG detection success rate may be obtained between the first line and higher of the second and third lines.

Advantageously, the electrodes arranged on the multi-electrode patch may define a rectangular, elongated or crescent electrode contact area. Step c) may then include aligning the at least three electrodes such that the longitudinal axis of each electrode contact area is substantially perpendicular to the abdominal muscle of the subject.

As previously discussed, such electrode alignment reduces the effects of noise caused by parasitic EMG signals on the detected signal, increasing the ability of the fECG monitor to extract the fECG signal.

In alternative embodiments the electrodes arranged on the multi-electrode patch define a substantially circular electrode contact area.

There now follows a description of preferred embodiments of the invention, by way of non-limiting examples, with reference being made to the accompanying drawings in which.

Figure 10B:
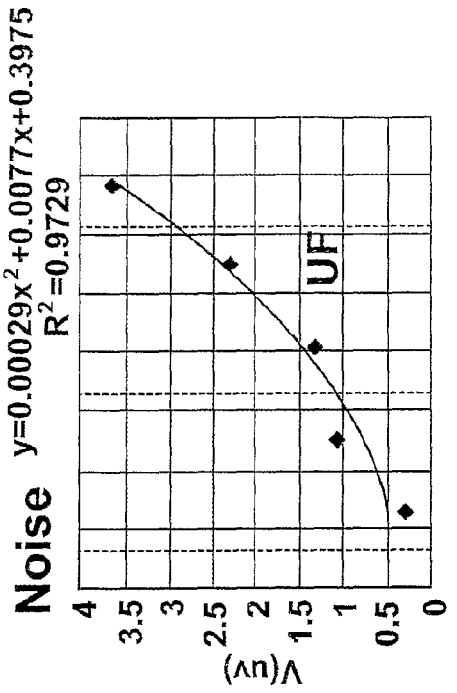
Figure 10A:
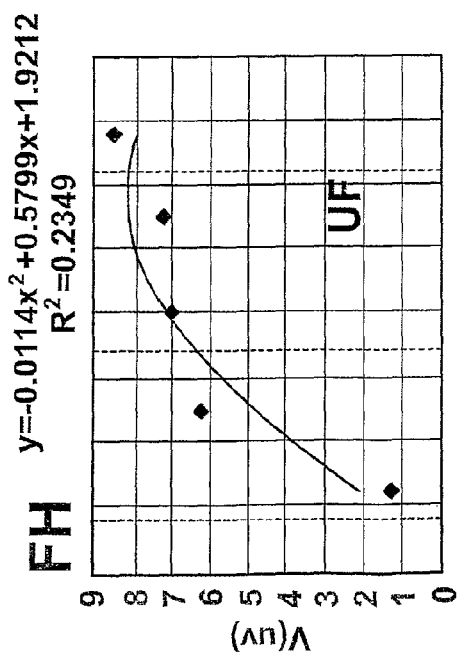
Figure 10C:
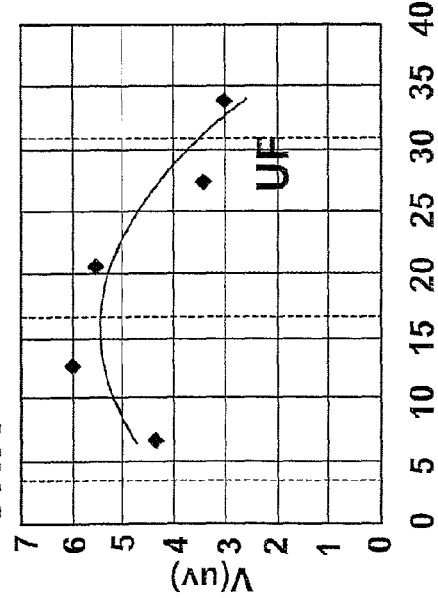
Figure 11A:
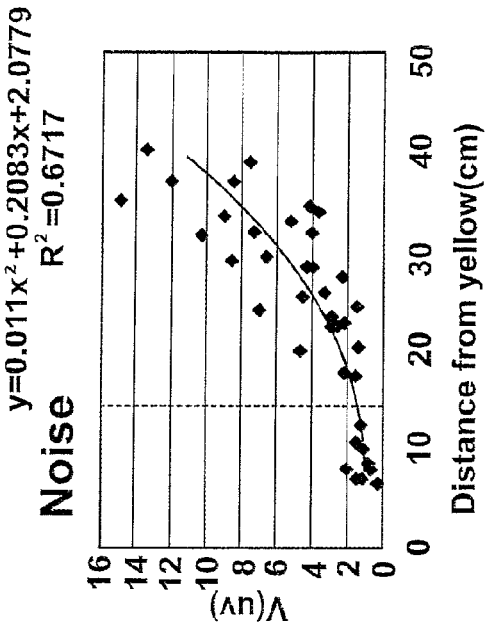
Figure 11B:
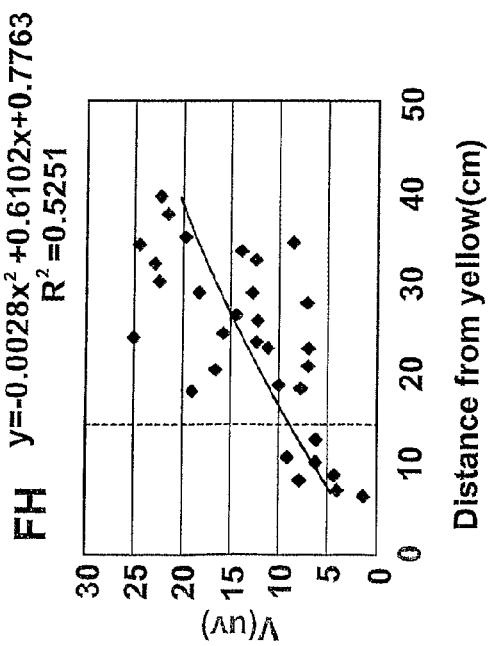
Figure 11C:
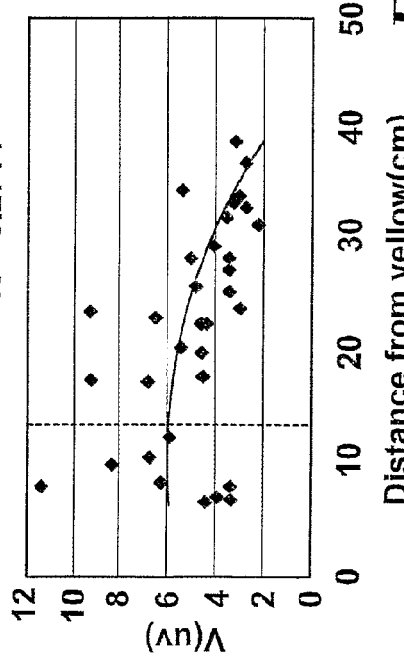
Figure 12A:
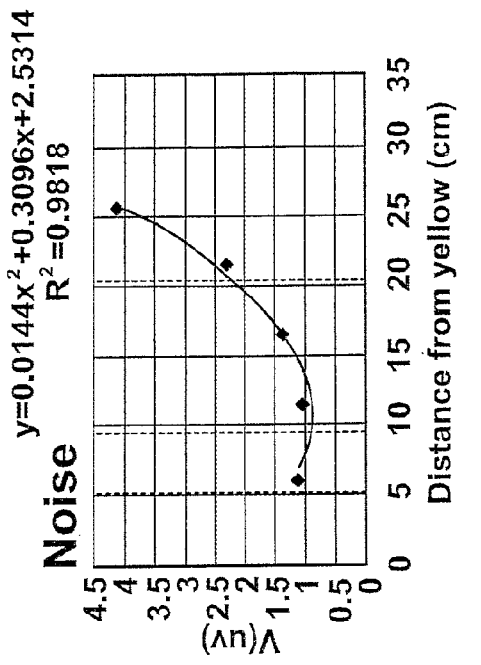
Figure 12B:
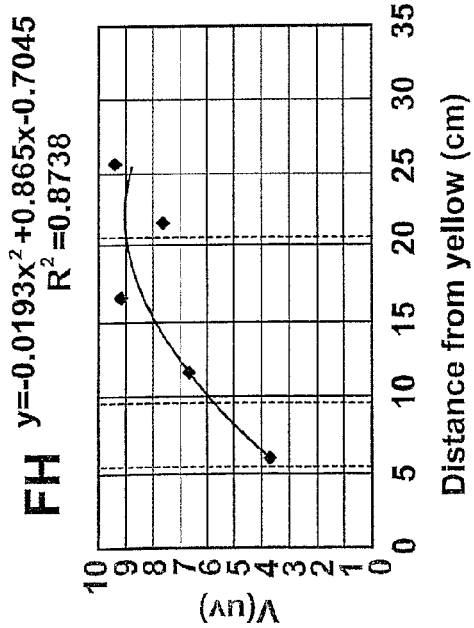
Figure 12C:
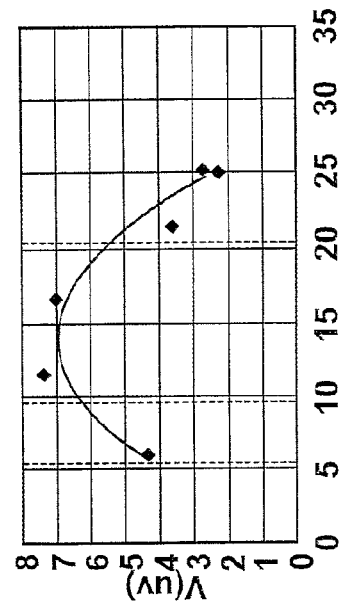
Figure 13A:
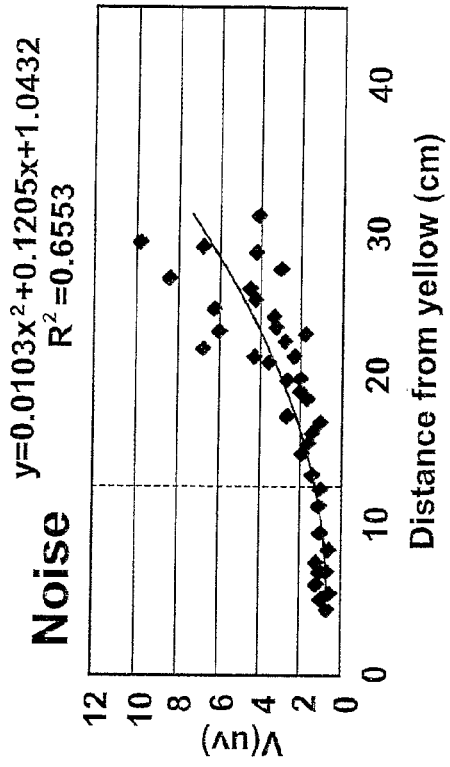
Figure 13B:
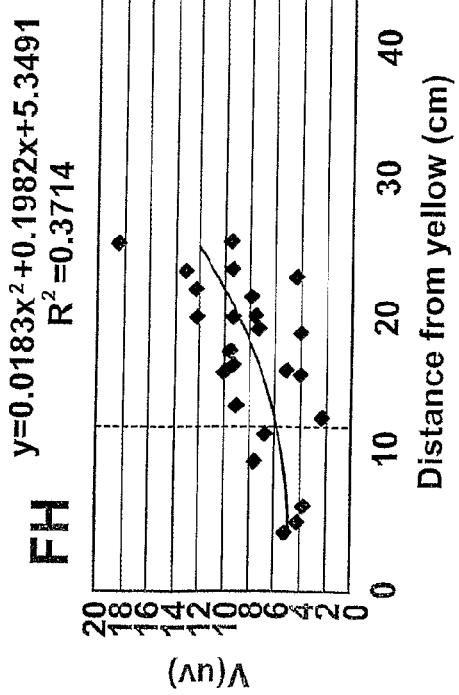
Figure 13C:
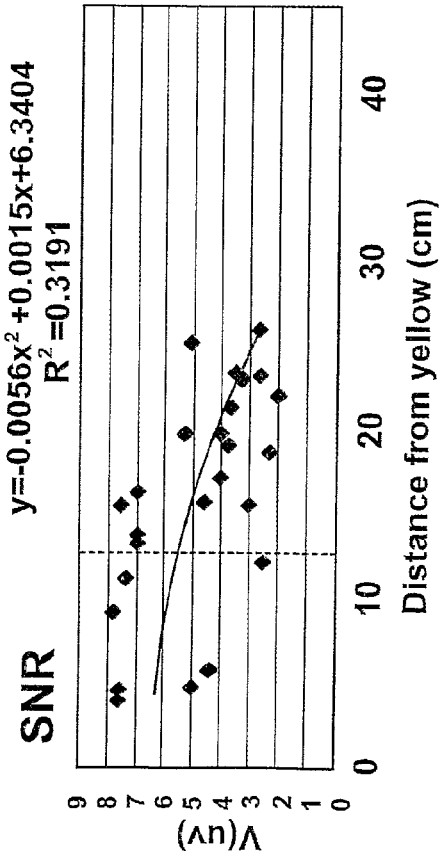
Figure 14A:
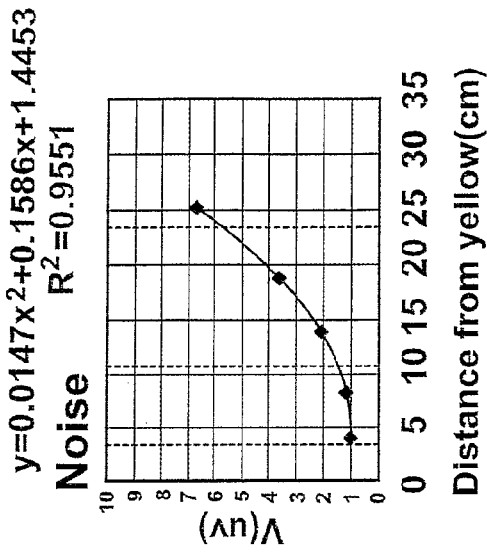
Figure 14B:
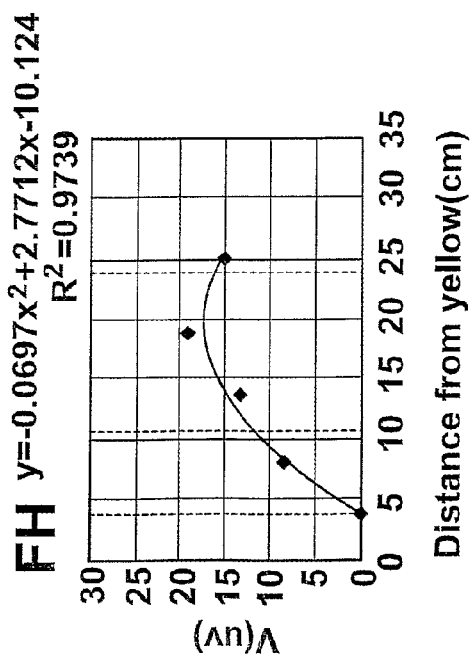
Figure 14C:
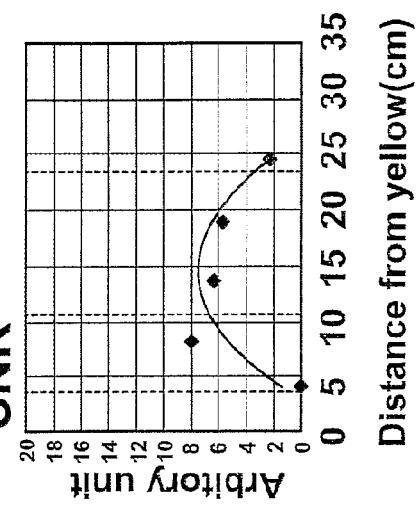
Figures 15A, 15B, 15C:
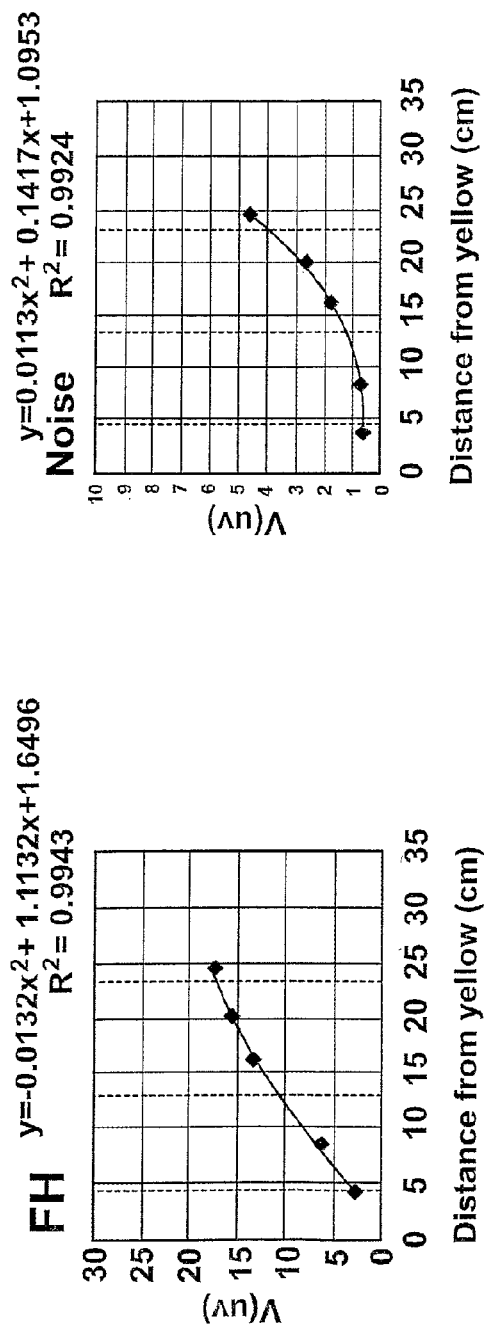

FIGS. 10a, 10b and 10c respectively show fetal signal height, noise and signal-to-noise ratio as a function of electrode position on a line from the symphis pubis vertically to the Xiphoid process, for a 38 week gestational mother FIGS. 11a, 11b and 11c respectively show fetal signal height, noise and signal-to-noise ratio as a function of electrode position on a line from the symphis pubis vertically to the Xiphoid process, for ten different mothers with gestational ages greater than 37 weeks;

FIGS. 12a, 12b and 12c respectively show fetal signal height, noise and signal-to-noise ratio as a function of electrode position on a line from the symphis pubis vertically to the Xiphoid process, for a 30 week gestational mother;

FIGS. 13a, 13b and 13c respectively show fetal signal height, noise and signal-to-noise ratio as a function of electrode position on a line from the symphis pubis vertically to the Xiphoid process, for ten different mothers in the vernix period with gestational periods in the range 29 to 32 weeks;

FIGS. 14a, 14b and 14c respectively show fetal signal height, noise and signal-to-noise ratio as a function of electrode position on a line from the symphis pubis vertically to the Xiphoid process, for a 35 week gestational mother; and FIGS. 15a, 15b and 15c respectively show fetal signal height, noise and signal-to-noise ratio as a function of electrode position on a line from the symphis pubis vertically to the Xiphoid process, for a 35 week gestational mother.

Figure 2:
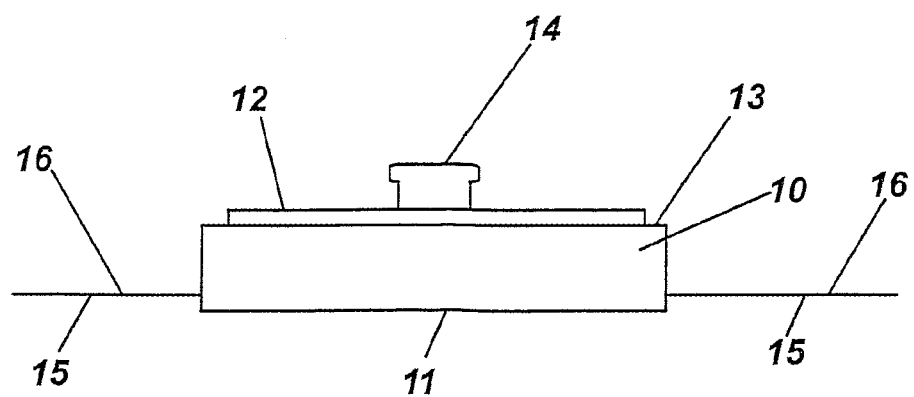
FIG. 2 shows a cross section through a wet gel electrode.

Referring to FIGS. 2 and 3 a wet gel electrode includes a gel contact 10. An electrical conductor 12 is positioned on top of the gel contact 10 so as to effect electrical communication between the gel contact 10 and the electrical conductor 12.

The gel contact 10 consists of a saline gel solution held within a sponge. The electrical conductor 12 is a silver/silver chloride film.

A lower surface 11 of the gel contact 10 defines an electrode contact region. The electrode contact region is in contact with the skin when the electrode is attached to a pregnant subject. In preferred embodiments of the invention the lower surface 11 of the gel contact has a rectangular or elongated shape. However, in other embodiments the lower surface 11 of the gel contact may define an electrode contact area of another shape e.g. circular, elliptical, crescent (i.e. banana shaped) or square.

A rectangular or elongated lower surface 11 of the gel contact 10 can be used to reduce larger parasitic EMG signals which may otherwise be present on the fECG signal. The elongate electrode may be deployed on the maternal abdomen such that a longitudinal axis of the electrode is transverse, and preferably substantially at right angles to, the abdominal muscles of the subject. (For certain muscle arrangements on the abdomen this may require alternative elongated shapes i.e. a crescent shape). This results in a reduced spatially averaged EMG signal and will transform the signal into a synchronously arriving EMG signal thereby allowing other parts of the detected signal to reveal the fECG signal without interference from the EMG signal.

In one preferred embodiment, the electrode contact area is greater than 370 square millimeters. In another preferred embodiment the electrode contact area may be greater than 490 square millimeters. However, the electrode contact area may be of varying sizes including e.g. greater than 400 or greater than 450 square millimeters.

The interface between the gel contact 10 and the electrical conductor 12 is a physical connection. The gel contact 10 is adhered to the substructure 16 around the outside of the electrical conductor 12 on the gel contact periphery 13 and hence these elements are held intimately together.

Attached to and in electrical communication with the electrical conductor 12 is a connector 14. The connector 14 is a male portion of a stud connector capable of connection to a reciprocal female portion (not shown). Connection of the electrode to a fetal ECG monitor such as the Monica AN24 is either directly via the connector 14 or through the flat flexible cable.

Figure 3A:
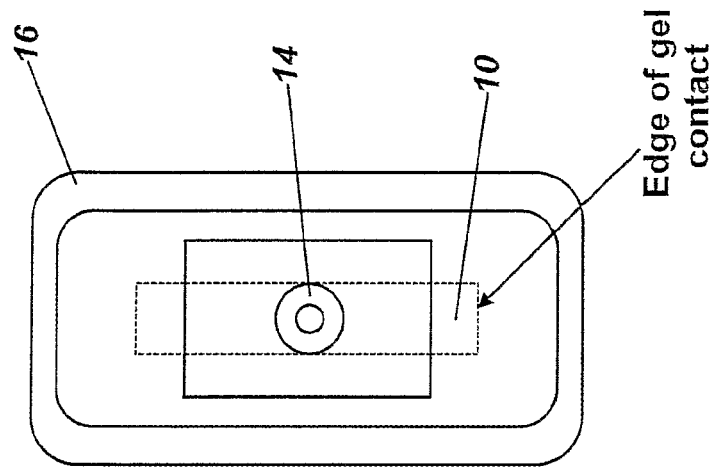
FIG. 3a shows a plan view of a rectangular wet gel electrode.
Figure 3B:
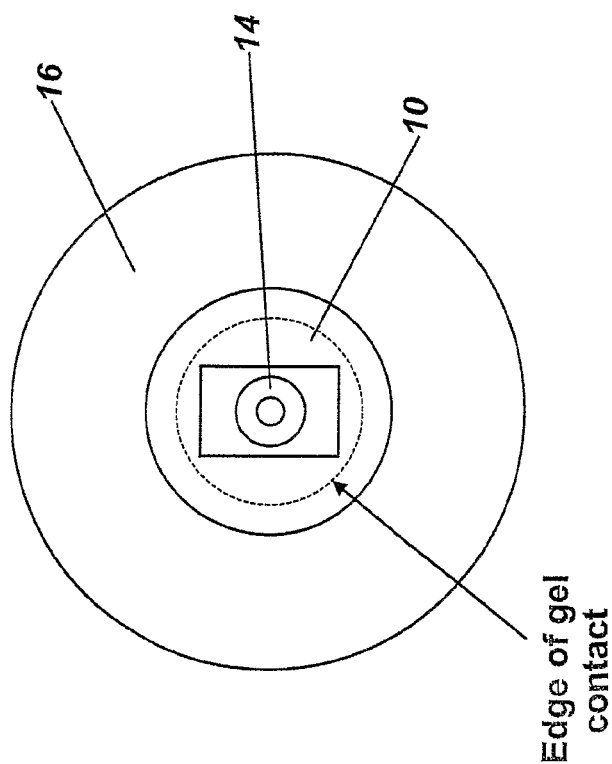
FIG. 3b shows a plan view of a circular wet gel electrode.
Figure 3C:
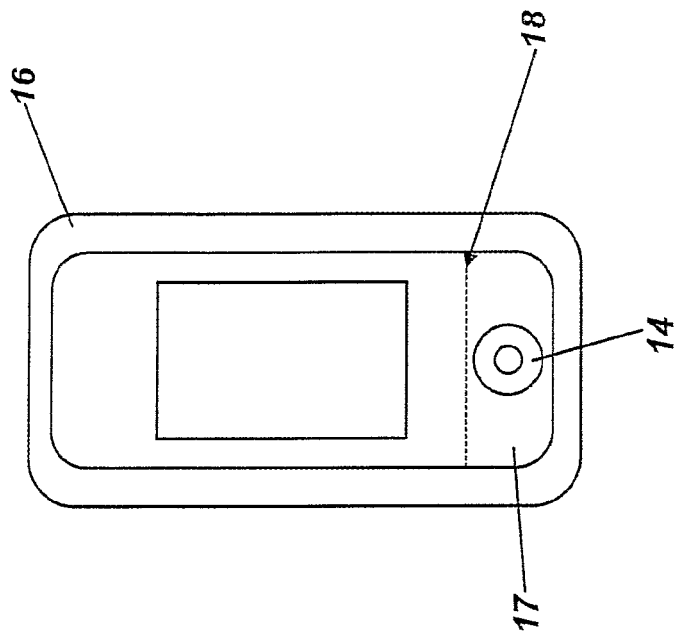
FIG. 3c shows a plan view of a rectangular electrode with offset electrode connector.
Figure 3D:
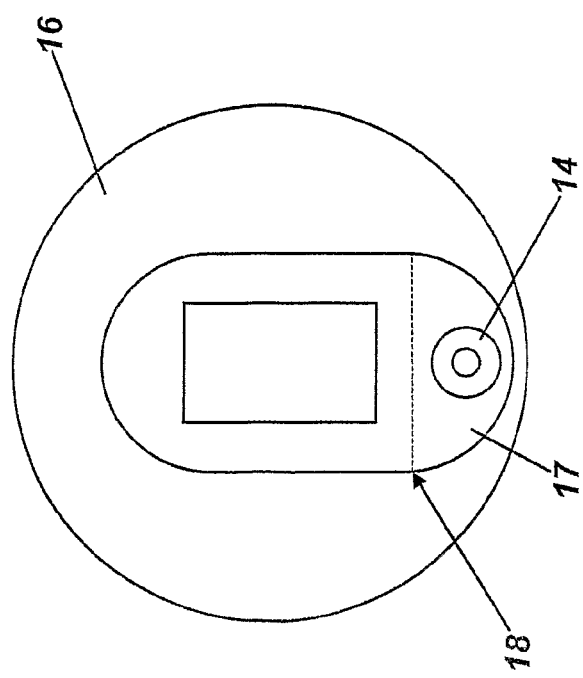
FIG. 3d shows a plan view of a circular electrode with offset electrode connector.

Whilst the connector 14 is a stud connector, other types of connector may alternatively be used. These can include push fit IDC (Insulation Displacement Connector), low insertion force connectors, zero insertion force connectors, in line banana plugs, offset tab connector (in the case of offset ECG stud electrodes), push through displacement connectors, or in the case of the flat flexible cabling a direct electrical connection. Alternatively, connector 14 can be an offset connection whereby the electrode stud is positioned on a piece of metal that extends from the centre of the electrode out to the side as shown in FIGS. 3c and 3d. This type of electrode has the following advantages: it allows the connection of cabling without pressing on the centre gel and hence protects the integrity of the gel when applied to the mother; it means that the mother's abdomen is not pressed unnecessarily whilst applying the connection; it results in a reduced motion artefact from tugging cables since the cable is not at the centre but at the offset edge away from the gel contact region accessed via a strain relief hinge. The electrode includes a substructure 16 connected to the electrical conductor 12 and the gel contact 10. This physical substructure can be a soft cloth or foam backed plastic such that it allows the gel contact 10 to be adhered around the gel contact periphery 13. The lower surface 15 of the substructure 16 has a biocompatible adhesive that adheres to the skin surface and ensures that the electrode is held firmly in place on the pregnant subject.

In one embodiment of the invention the substructure 16 is rectangular in shape. The substructure 16 overlays the gel contact 10, the electrical conductor 12 and the connector 14. A male and female stud can be used that allows the stud to penetrate through the substructure and a mating stud is clipped on top that grips to both the underlying stud and the surrounding substructure. Alternatively, the substructure 16 may include a cutaway section to expose the connector 14 and allow connection to an fECG monitor.

The substructure 16 extends laterally beyond the lower surface 11 of the gel contact 10 preferably on all sides. The lower surface 15 of the extended portion of the substructure may preferably be coated in a biocompatible adhesive suitable for attaching the substructure to the skin of a pregnant subject.

The electrode may be attached to the maternal abdomen using the adhesive coated onto the lower surface 15 of the substructure. Attachment of the electrode in this way places the lower surface 11 of the gel contact 10 in contact with the skin of the maternal abdomen. The electrode can then be connected to a suitable fECG monitor via the connector 14 establishing an electrical sensing link between the skin of the pregnant subject and the fECG monitor.

Connector 14 is located in the centre of the electrode. In other embodiments the connector 14 can be an offset connector as illustrated in FIGS. 3c and 3d where connector 14 is located on a hinged tab 17. The hinge is represented in FIGS. 3c and 3d by dashed line 18. These types of connections have advantages over the centre connector as follows: if the electrode is placed on the skin first the gel is not displaced when the ECG stud is applied; an electrode with an offset connector does not require pressure to be placed on the skin and hence the fetus; the offset connector reduces artefact caused by ECG stud cable lifting/modifying the gel contact and hence changing the contact impedance.

The issue related to this aspect is that local movement of the gel contact 10 can generate artefactual differential electrical signals which can create noise or if transient contact impedance occurs then can even masquerade as a fetal ECG signal. With the offset connector a hinged tab 17 exists which acts as a strain relief and dramatically reduces the motion artefact over the contact gel. The hinged tab 17 may be lifted away from the upper surface of the substrate 16 so that a finger may be placed under the tab. This provides a surface against which pressure required to connect the stud can be applied. To prevent the hinged section from suffering with triboelectric and electrostatic effects the underneath of the hinged offset tab is often coated in graphite or other similar conducting materials.

The size of the contact area of an electrode has a significant effect on the noise associated with the electrode and the signal-to-noise ratio of any signals detected by the electrode. If the contact area is increased, and the resistivity and depth of the gel contact 10 remain the same, the signal-to-noise ratio of the detected signal will increase.

Based on the relationship between noise and electrode contact region given previously, and assuming that the resistivity of the gel contact 10 remains constant, if the electrode contact area is doubled the signal-to-noise ratio is increased by a factor of $\sqrt{2}$. If the electrode contact area is trebled the signal-to-noise ratio is increased by a factor of $\sqrt{3}$.

Typically adult ECG wet gel electrodes have an area of around 284 square millimeters. Therefore, the increased size of the electrode contact area of the invention to 370 square millimeters results in an improvement of 15% in the signal-to-noise ratio over an adult ECG wet gel electrode.

The increase in area could be used to reduce the amount of skin preparation required to achieve the same signal-to-noise ratio as that achieved with a smaller electrode. An increase in area from 284 to 370 square millimeters represents approximately a 30% increase in area. This area increase results in a reduction in skin preparation.

For example, current methods of skin preparation used with adult ECG wet gel electrodes of 284 square millimeters in area typically requires 10 strokes of "skin prep" abrasive paper, manufactured by 3M, to prepare the skin surface and achieve an acceptable impedance of less than 2,000 ohms and hence an acceptable signal-to-electrode noise ratio. The action of abrading the skin surface is to remove the stratum corneum (SC) layer which has a very high resistivity of the order of $9 \times 10^6$ ohm centimeters. Given that the SC is approximately 100 micrometers in thickness then this corresponds to a contact resistance at each electrode of approximately 40,000 ohms. Hence, in order for the electrode to make a good contact then this SC must be removed underneath the electrode. By abrading the skin the SC will gradually be punctured and the number of holes in the SC will increase as skin prep is increased. If we assume that the number of holes per $cm^2$ is H and the area of the electrode is A then the chances of one of the holes lying under the electrode is given as (1−Y), where Y is given by Murphy's model semiconductor defect equation namely:

$$Y = \left( \frac{1 - e^{-AH}}{AH} \right)^2 \qquad \text{Equation 4}$$

Figure 7A:
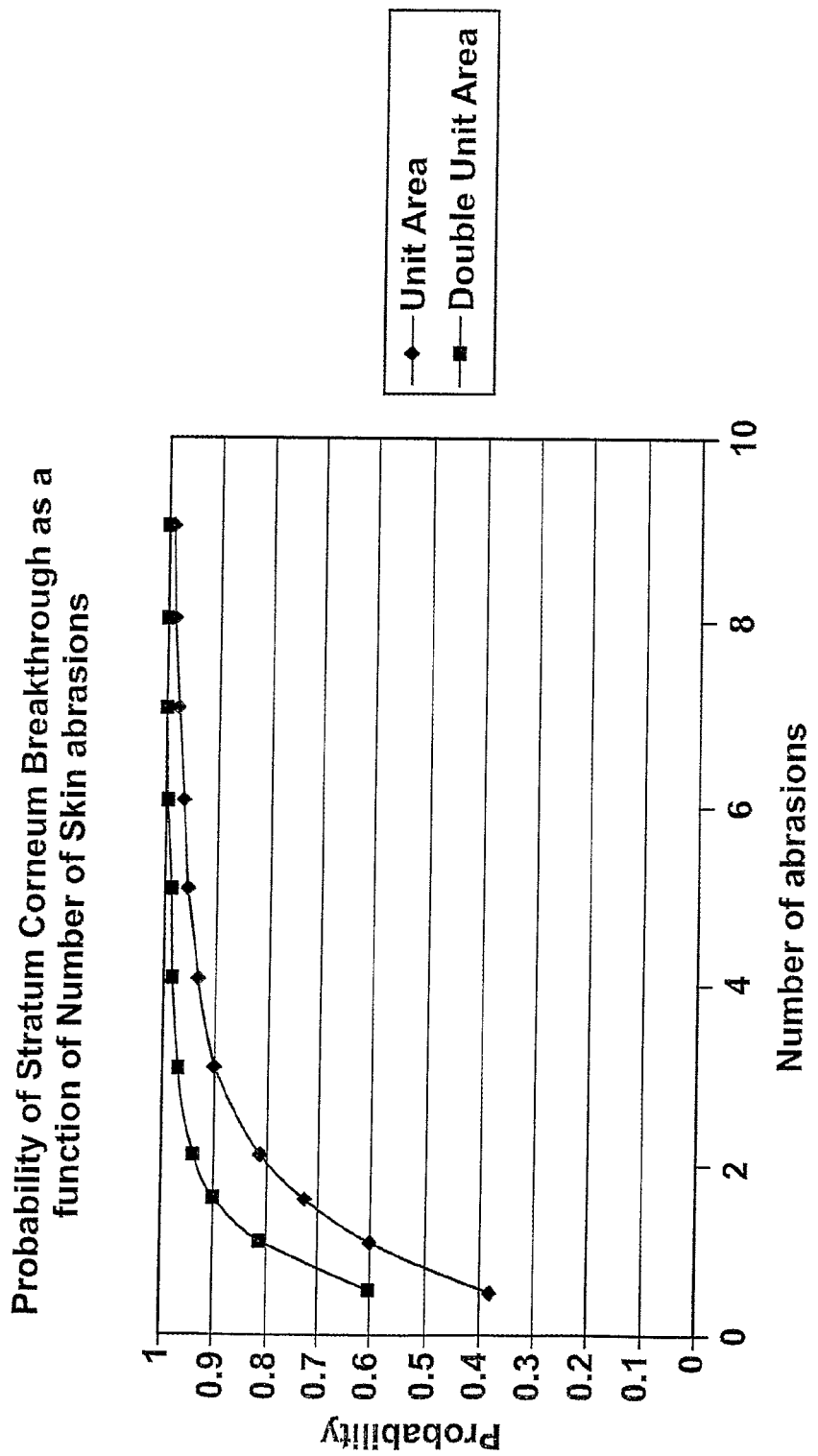
FIG. 7a shows the probability of stratum corneum breakthrough as a function of the number of skin abrasions.
Figure 7B:
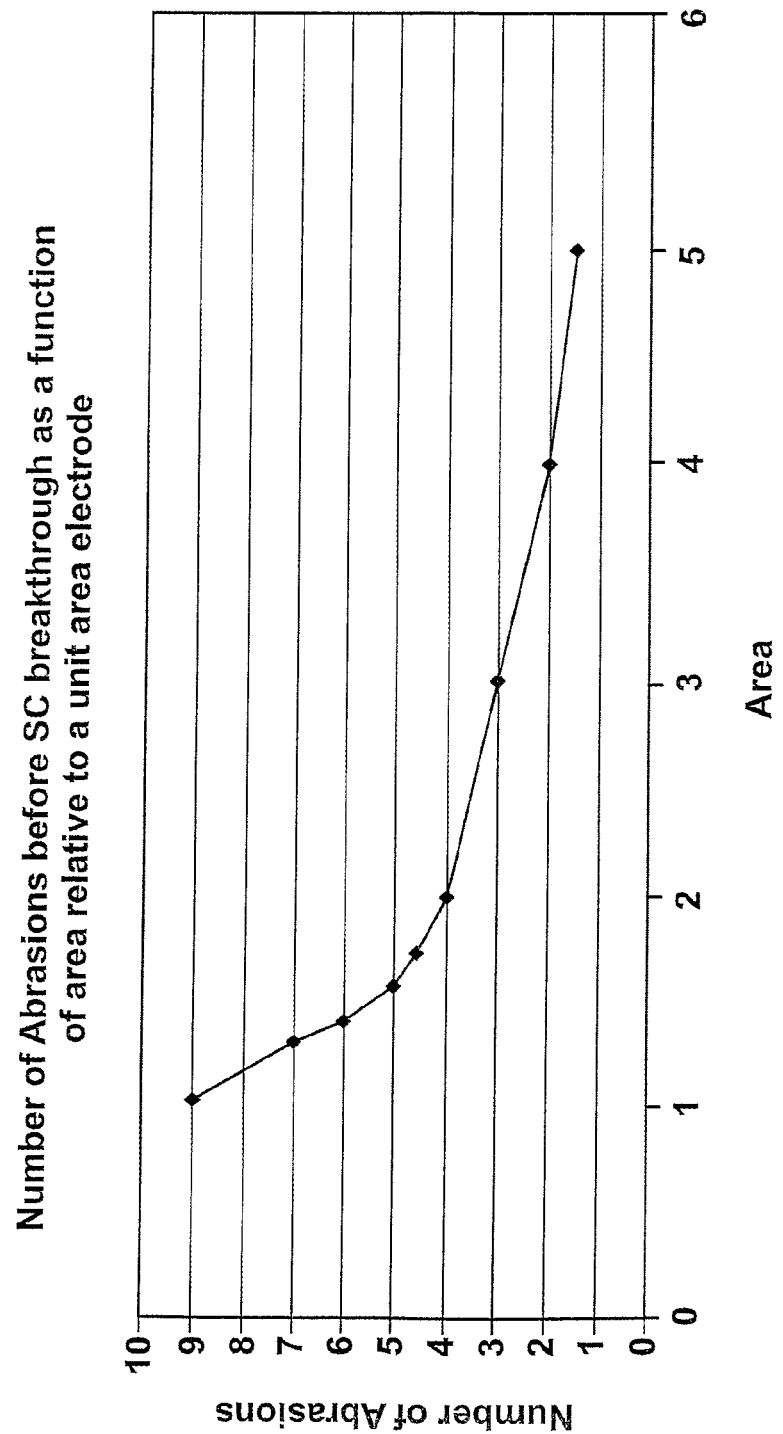
FIG. 7b shows the number of skin abrasions required before stratum corneum breakthrough as a function of area relative to a unit area electrode.
Figure 7C:
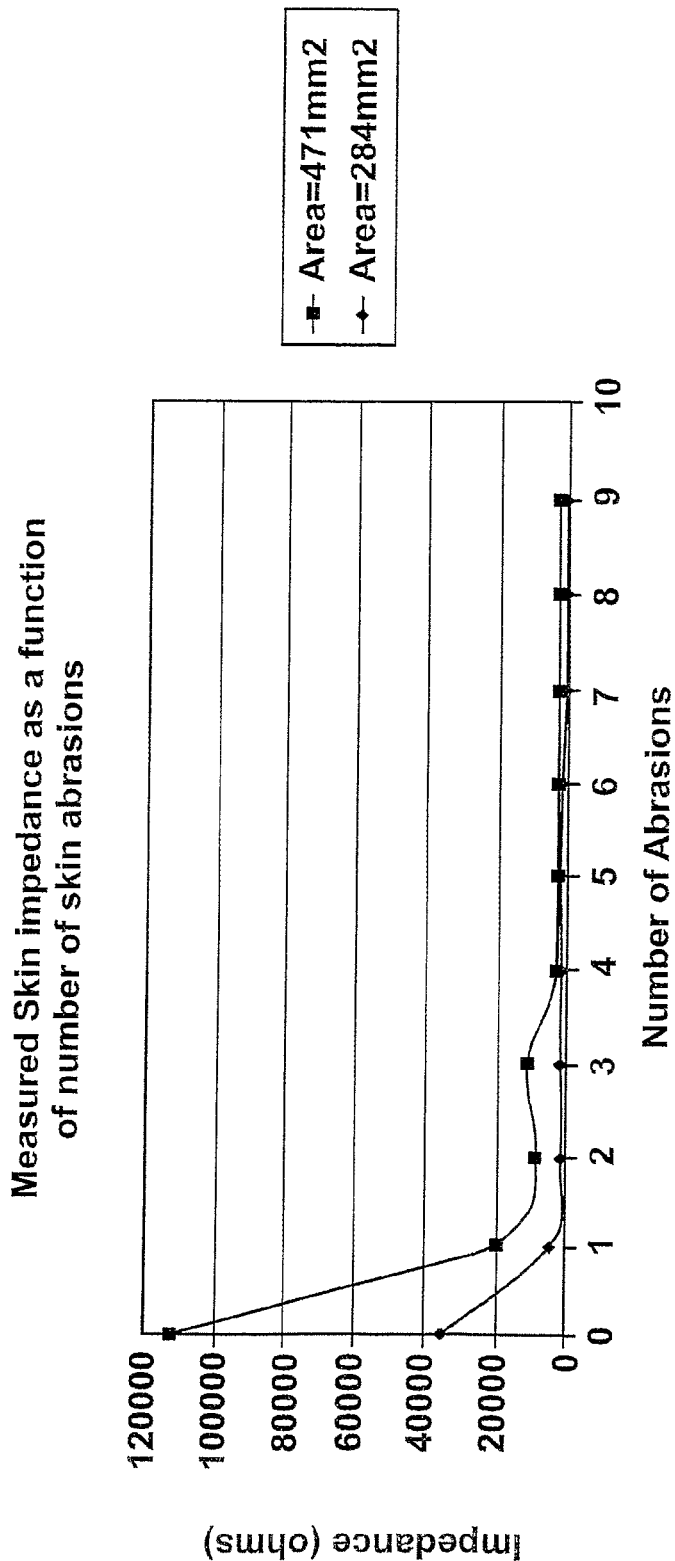
FIG. 7c shows measured skin impedance as a function of the number of skin abrasions.

The larger the area then the greater the chance of the electrode lying over an SC void. Or alternatively as the number of abrasions is increased then a larger area electrode will have an even greater chance of connecting to the underlying dermis layer. However, this relationship, modelled from Equation 4, is not linear as is shown in FIGS. 7a to 7c. For example FIG. 7a shows the probability of penetrating the SC increases with increasing abrasion. The two traces refer to two different areas one being the double of the other. FIG. 7a shows that as the area is doubled the chance of missing the void (i.e. 1−Y axis) does not increase linearly with the doubling in area for each number of abrasions. This is reinforced by FIG. 7b which shows the number of abrasions needed (D) for varying area in order to achieve the same probability of void coincidence. Here we see again a non linear relationship "bottoming out" at approximately 1 abrasion for very large areas. Finally, FIG. 7c shows measured results on electrode impedance as a function of the number of abrasions. Again a non-linear relationship can be seen and for an area of 284 $mm^2$ 9 abrasions are needed in order the get the impedance down to 2,000 ohms. However, for an electrode of area 471 $mm^2$ then in order to reach the same impedance only 4 abrasions are needed.

From these graphs it can be seen that using an electrode contact area increased by 30% would allow a drop in the required skin preparation of from 9 strokes to 7 strokes of the abrasive paper to achieve similar signal-to-noise ratio.

In certain embodiments the electrode contact area may be 400 square millimeters, resulting in an improvement in the signal-to-noise ratio of 19% or a reduction in skin preparation to 6 abrasions.

In further embodiments the electrode contact area may be 450 square millimeters, resulting in an improvement in the signal-to-noise ratio of 26% or a reduction in skin preparation to 5 abrasions.

In yet further embodiments the electrode contact area may be 490 square millimeters, resulting in an improvement in the signal-to-noise ratio of 31% or a reduction in skin preparation to 4 abrasions. However, for fully intact SC it would normally be necessary to create at least one void in the SC and hence at least one skin abrasion would normally be required.

Taking this to the limit of creating a very large electrode does not result in a simple linear increase in signal to noise ratio. This is because the fECG signal is not present in equal measure over the entire maternal abdomen. Therefore, if electrode contact regions are too large, the averaged fECG signal strength may reduce when the electrode contact region includes an area of the maternal abdomen where the fECG signal is small or not detectable.

Measurements performed on over 400 patients have shown that the fetal ECG can vary significantly across the abdomen. It is found that with the position of the electrodes' centres being 140 mm apart (see FIG. 5) the fetal ECG is often present on one electrode but not on the other. Hence an upper limit to the size of the electrode may be an area of approximately 1600 $mm^2$.

Figure 4:
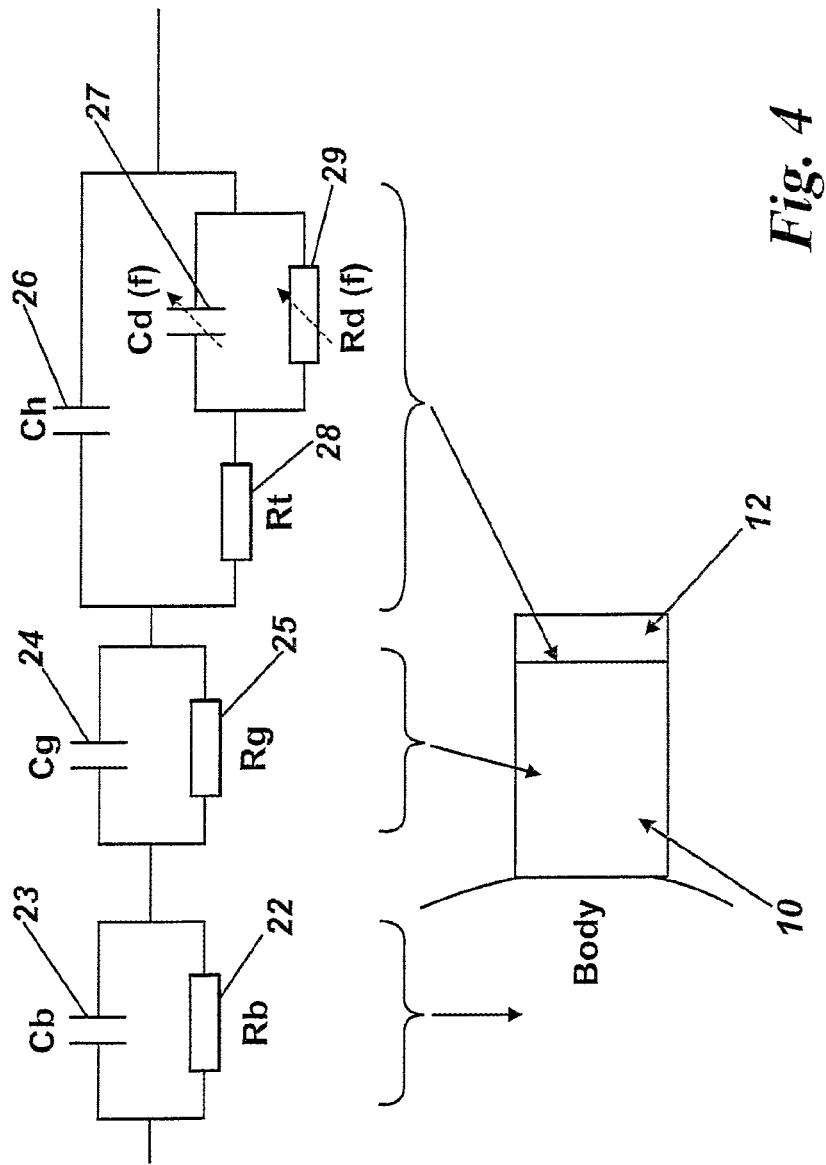
FIG. 4 shows a schematic representation of a wet gel electrode and its equivalent electrical circuit model.

FIG. 4 shows a schematic representation of a wet gel electrode according to the invention and its equivalent circuit model. In FIG. 4:

Cb is the capacitance of the body and organs 23;
Rb is the resistance of the body and organs 22;
Cg is the capacitance of the Gel layer 24;
Rg is the resistance of the Gel layer 25;
Rt is the AC small signal resistance of the space charge region 28;
Ch is the AC small signal capacitance of the space charge region 26;
Rd(f) is the frequency dependent AC small signal resistance of the diffusion region (Warburg resistance) ~$1/\sqrt{freq}$ 29; and
Cd(f) is the frequency dependent AC small signal capacitance of the diffusion region (Warburg capacitance) ~$1/\sqrt{freq}$ 27

The schematic representation of the wet gel electrode shows the electrical conductor 12 connected to the gel contact 10. The gel contact 10 is in contact with the skin of the subject 20.

The impedance of the subject's body is represented in FIG. 4 by resistor 22 and capacitor 23. The impedance of the gel contact 10 is represented in the equivalent circuit model by capacitor 24 and resistor 25. The impedance of the interface between the gel contact 10 and the electrical conductor 12 is modelled by the portion of the equivalent circuit model containing capacitances 26 and 27 and resistors 28 and 29.

Increased electrode contact region reduces the resistance 25 of the gel contact 10. A similar effect occurs with reduction of the resistances 28 and 29. The overall effect will lead to a reduction in the overall impedance of the electrode and an increase in signal-to-noise ratio.

The typical value of saline gel concentrations is 1% to 5% salt however, higher salt concentrations can be used on the larger area electrode and an even further reduction in the electrode noise occurs. However, increasing the saline concentration towards 15% can result in skin irritation with prolonged use and hence negate the technical advantage of a larger area electrode.

As discussed above, use of wet gel electrodes is preferred over hydrogel electrodes for fetal ECG detection. Hydrogel resistivity is relatively high compared to wet gel and hence for the same unit area a wet gel electrode has much lower resistance. For high quality adult ECG electrodes the impedance needs to be typically 3000 ohms. In order to achieve this for hydrogel, a much larger area is necessary which can compromise the fECG signal quality. Wet gel electrodes improve this position since their resistivity is low and an impedance of 3000 ohms can be achieved without increasing the contact area diameter above ~18 mm.

For abdominal fetal ECG detection the signal is much smaller and hence is more vulnerable to noise. From Equation 1 the noise sources generate a noise current which passes through the electrode impedance, Z. The lower the value of Z, the lower the noise voltage.

Two problems therefore may occur in using large area hydrogel electrodes for abdominal fetal ECG:
1. The larger resistivity of hyrdrogel compared to wet gel requires a much larger area electrode to obtain an impedance below 3,000 ohms
2. Hydrogel electrodes have an inherently higher noise than wet gel for the same area electrode.

fECG signals are generally 100 to 1000 times smaller than adult ECG signals and wet gel electrodes advantageously achieve the required low resistance while avoiding problems that may arise with larger electrodes.

Figure 5:
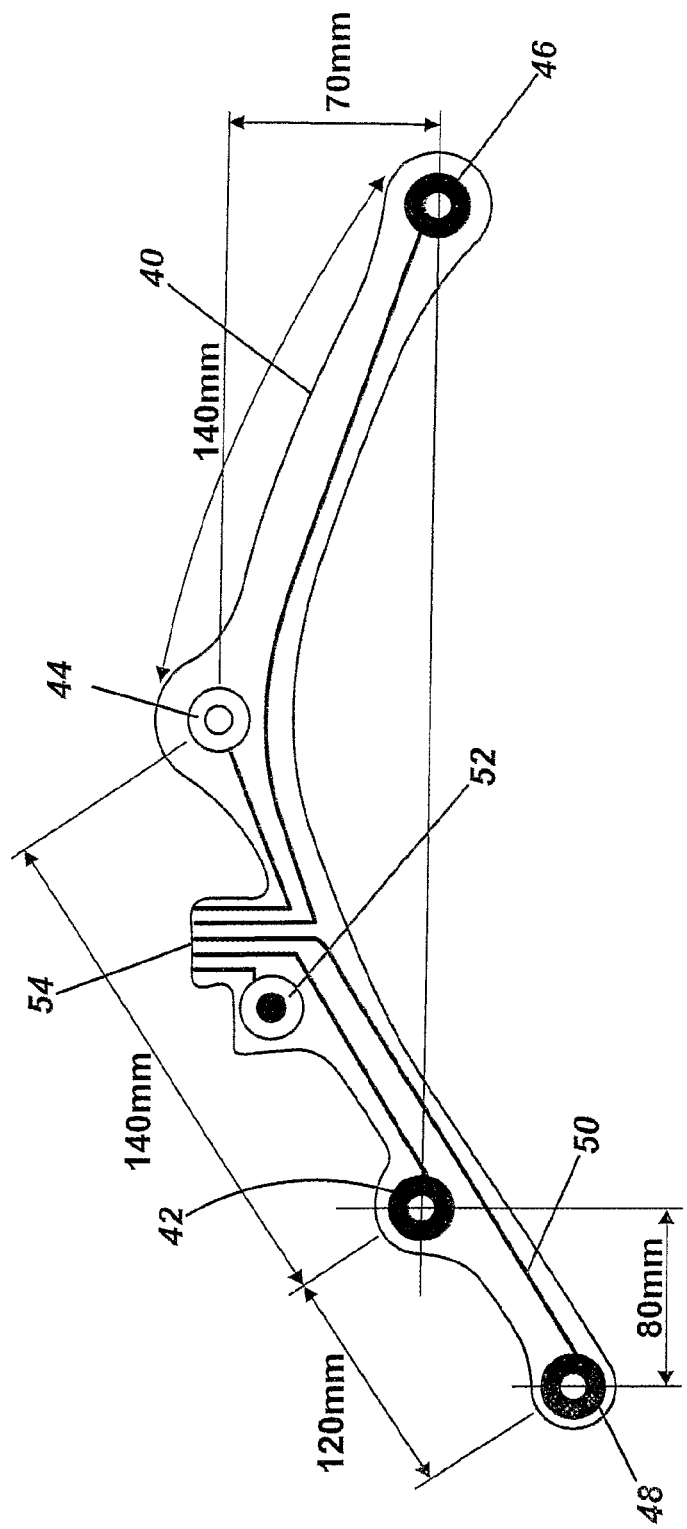
FIG. 5 shows a plan view of a multi-electrode patch.

FIG. 5 shows a multi-electrode patch according to the invention. The multi-electrode patch comprises a flexible substructure 40, which may be a flat flexible cable, on which are mounted three sensing electrodes 42, 44, 46 that approximate an arc. In certain embodiments of the invention more electrodes may be used to approximate the arc e.g. four electrodes, five electrodes or six electrodes. However, 3 detection electrodes is the preferred number along this arc.

The flexible substructure 40 may be generally flat in nature. As well as housing the cables which provide electrical communication between the electrodes 42, 44, 46 and the fECG monitor, the flexible substrate also restricts the relative positions in which the electrodes 42, 44, 46 may be placed. The flat nature of the flexible substrate enables it to resist bending in a plane defined by the upper and lower surfaces of the substructure 40.

A right leg driver electrode 48 is arranged on the flexible substructure 40 connected at the distal end of a spur 50. In some embodiments of the invention the right leg driver electrode may not be included on the patch but may be attached to a subject separately.

Figure 8:
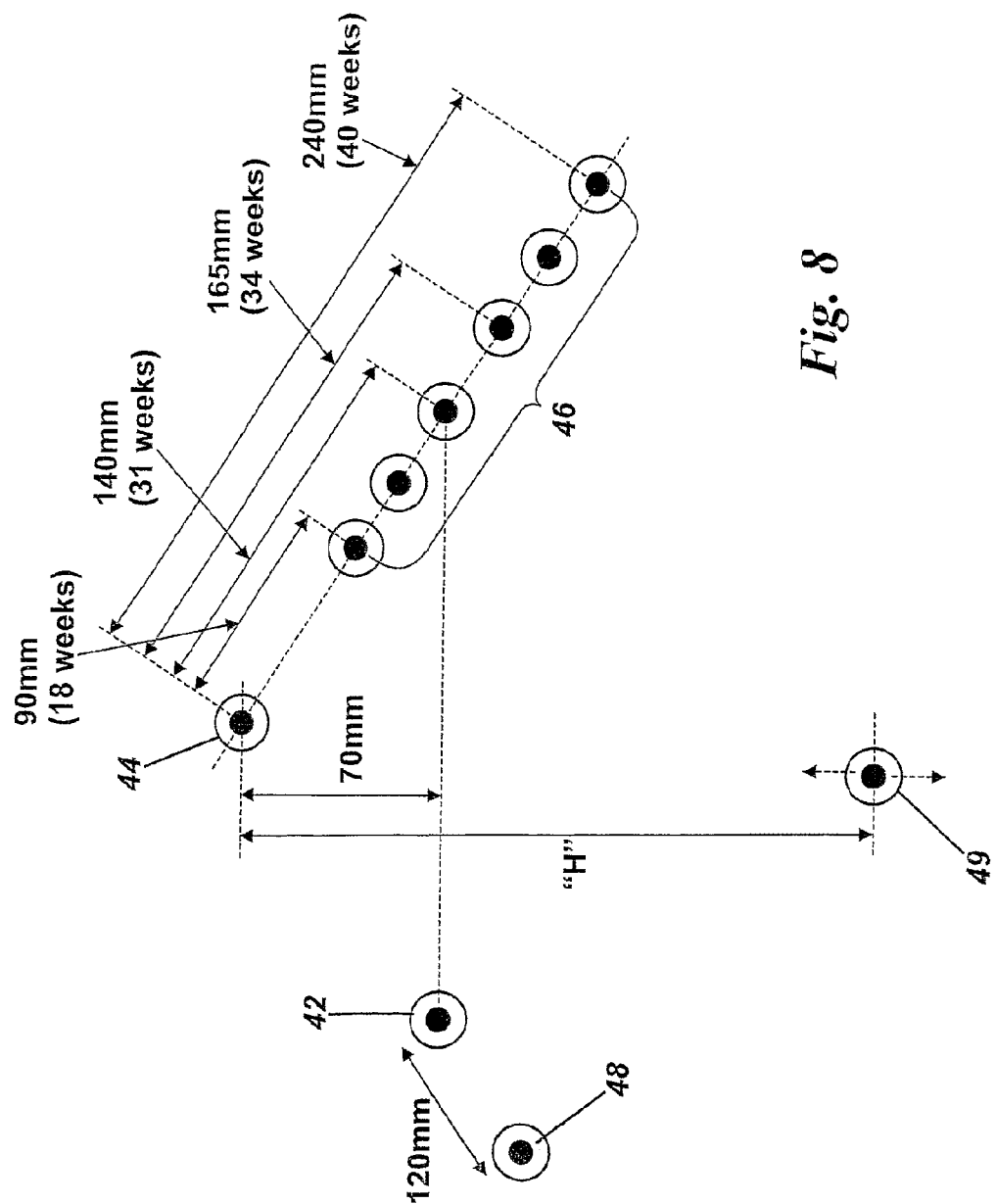
FIG. 8 shows the various electrode locations as a function of gestational weeks.

Optionally, a common electrode (not shown) may also be arranged on the flexible substructure 40. In the embodiment shown in FIG. 5, the common electrode is attached to the subject separately and connected to the multi-electrode patch at stud connector 52. A separate flat electrical cable carries the electrical signal from the common electrode at the symphysis pubis. Throughout gestation the electrode positions for electrodes 42, 44 and 46 do not vary significantly however, the common electrode at the symphysis pubis can vary significantly. FIG. 8 shows the relative positions of sensing electrodes 42 and 46 and the common electrode 49 as a function of gestation, all with respect to the centre electrode 44. The common electrode 49 may be disposed at a distance "H" from the centre electrode 44 as shown in FIG. 8.

Preferably, the electrodes 42, 44, 46, 48 arranged on the flexible substructure 40 are wet gel electrodes. However, the multi-electrode patch may include other types of electrode such as e.g. hyrdogel electrodes, dry electrodes and capacitive non-contact electrodes.

In a particular embodiment the electrodes 42, 44, 46, 48 include electrodes with an electrode contact area of greater than 370 square millimeters. In an alternative embodiment the electrodes 42, 44, 46, 48 include electrodes with an electrode contact area of greater than 490 square millimeters. However, other electrode contact areas may be used within the scope of the invention e.g. greater than 400 square millimeters or greater than 450 square millimeters.

Electrodes 42, 44, 46, 48 may advantageously be rectangular, elongated or crescent in their shape. This reduces the effects of interference from EMG signals produced in the muscles of the subject.

FIG. 8 shows the relative positions of electrodes 42, 44, 46 and 48 and the common electrode on the multi-electrode patch. The various positions of the electrodes are dependent on gestation time.

FIG. 8 shows the distances between electrode 46 and electrode 44 as a function of gestation time. Although it is not shown in FIG. 8, the distance between electrode 44 and electrode 42 will also vary as a function of gestation time.

The distances between electrode 44 and electrodes 42 and 46 may preferably be according to the information contained in the table below:

| Gestation Time (Weeks) | Distance of Electrodes 42 and 46 from Electrode 44 (mm) |
| --- | --- |
| 18 | 80 to 100 |
| 31 | 130 to 150 |
| 34 | 155 to 165 |
| 40 | 230 to 250 |

In particular embodiments of the invention the distance between electrode 44 and electrodes 42 and 46 is according to the information given in the table below:

| Gestation Time (Weeks) | Distance of Electrodes 42 and 46 from Electrode 44 (mm) |
| --- | --- |
| 18 | 90 |
| 31 | 140 |
| 34 | 165 |
| 40 | 240 |

In embodiments of the invention in which the multi-electrode patch includes the common electrode 49, the distance H between the common electrode and electrode 44 will also vary with gestation time. This variance is represented by the information in the table below:

| Gestation Time (Weeks) | Distance of Common Electrode 49 from Electrode 44 (mm) |
| --- | --- |
| 18 | 180 to 200 |
| 31 | 290 to 310 |
| 34 | 330 to 350 |
| 40 | 390 to 410 |

In certain embodiments of the invention the distance H between the electrode 44 and common electrode 49 is according to the information given in the table below:

| Gestation Time (Weeks) | Distance of Common Electrode 49 from Electrode 44 (mm) |
| --- | --- |
| 18 | 190 |
| 31 | 300 |
| 34 | 340 |
| 40 | 400 |

In another embodiment of the invention the right leg driver electrode 48, located on the spur portion of the patch, is located a distance of 120 mm from electrode 42.

Typically, the height of the uterus fundus above the symphis pubis will vary as a function of gestation time. The information given in the table below shows this variance in height and is taken from "Symphysis fundal height curve—a simple method for foetal growth assessment" Rai L, Kurien L, Kumar P, Journal of PG medicine, 1995, vol 41 issue 4, pp 93-94.

| Gestation Time (Weeks) | Height of Uterus Fundus Above the Symphis Pubis (cm) |
|---|---|
| 20 | 19 +/− 1.3 |
| 24 | 23 +/− 1.9 |
| 28 | 27 +/− 1.5 |
| 32 | 31 +/− 1.2 |
| 36 | 34 +/− 1.1 |
| 38 | 36 +/− 1.1 |
| 40 | 37 +/− 1.0 |

Each of the electrodes is electrically connected via shielded wires to a connection port 54. The connection port provides connectability to an fECG monitor.

In certain embodiments of multi-electrode patch additional sensing electrodes may be included. Preferably there may be a plurality of sets of additional sensing electrodes, each at predetermined positions on the flexible substructure relating to a number of different gestation times. Once the multi-electrode patch of this type is applied to a pregnant mother's abdomen, the operator can then connect a particular combination of sensing electrodes to the fECG monitoring device. The combination of sensing electrodes may correspond to the gestation time of a particular subject or may be selected to provide the greatest chance of detecting a fECG signal.

It will be appreciated that the embodiments described above may be defined in a general sense as a multi-electrode patch including at least one additional sensing electrode positioned on the line of the arc defined by the at least three sensing electrodes and spaced from a central electrode of the at least three sensing electrodes at a distance different to the spacing of the at least three sensing electrodes.

An exemplary multi-electrode patch according to this embodiment may comprise electrodes at any combination of the relative positions shown in FIG. 8 and tabulated above. A multi-electrode patch of this configuration allows a single patch type to be used on subjects of varying gestation times.

The interconnecting wires may be integrated into the flexible substrate so as to form a flexible flat cable. This structure lends itself to several advantages for the detection of low level signals on a pregnant mother. These advantages include:
- the application of a shield is straightforward and can either be the driven common mode voltage or simply a ground line;
- the triboelectric/inductive coupling effect is significantly reduced as the flat cable is not so easily bent as in a normal cable and is not held in a moving coaxial cable that has a plastic and movable metal sheath;
- with normal cables a loop often exists (see FIG. 1) between the common electrode cable and the three electrodes 42, 44 and 46—this is not possible in the flat flexible structure since the cable is placed in contact with the mother.

The shielding layer can either be on both sides of the patch or simply on the top side since the mother can provide a natural shield.

In one embodiment the flexible substructure 40 may preferably have an adhesive coating on its lower surface. The adhesive coating provides for attachment to the skin of a subject. In another embodiment the adhesive of the electrodes themselves can often suffice to hold the patch onto the mother's abdomen.

The multi-electrode patch of the invention is applied to the body of the skin in the region of the line of the uterus fundus of a pregnant subject. The line of the uterus fundus can be established by clinicians through palpation of the maternal abdomen and is well documented.

Once the line of the uterus fundus has been established the multi-electrode patch is placed on the pregnant subject such that the electrodes 42, 44, 46, that approximate the arc are situated no lower than the established line.

A second line may be established that is parallel to the line of the uterus fundus and passes through the Xiphoid Process of the subject. The multi-electrode patch may then be placed such that the electrodes 42, 44, 46 are situated on the subject's skin between the line of the uterus fundus and the second established line.

A common electrode is then placed on the subject's skin at a location approximating the symphis pubis. In embodiments where this electrode is not integrated into the flexible substructure 40 of the multi-electrode patch the common electrode is connected to the common input of a fECG monitor separately.

fECG signals can then be detected using the multi-electrode patch arrangement and a suitable low noise fECG monitor apparatus.

Preferably, a further electrode 48 is attached to the back or abdominal side of the subject to be used as a right leg driver. This electrode 48 may be integrated into the flexible substructure 40 as shown in FIG. 5 or may alternatively be a discrete electrode attached to the subject separately.

Figure 6:
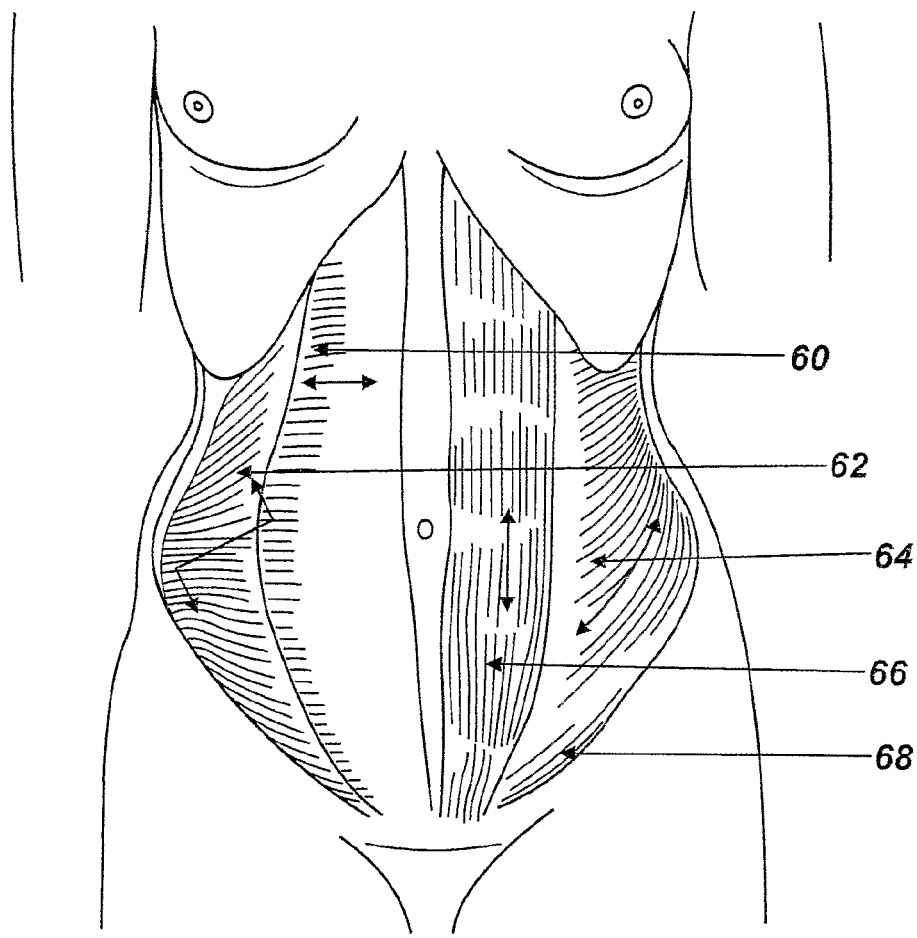
FIG. 6 shows a section through the human abdomen and the direction of the abdominal muscles.

FIG. 6 shows the direction of the muscles of the abdomen including the transversus abdominus 60, the internal oblique 62, the external oblique 64, the rectus abdominus 66. Fat and skin 68 is also depicted.

The arrows depicted on each muscle group of the abdomen in FIG. 6 show the direction of the muscle tissue in each muscle group.

The electrodes 42, 44, 46 of the multi-electrode patch may preferably define rectangular, elongated or crescent electrode contact areas. These electrodes may be placed on the subject's abdomen such that the longitudinal axis of the electrode contact area is transverse to, or preferably orthogonal to, the direction of the muscle tissue muscles of the subject's abdomen.

This configuration will advantageously reduce the effects of noise introduced on the detected signal caused by parasitic EMG signals.

The electrode patch may also include integrated circuitry configurable to amplify and filter a detected fetal electrocardiogram signal. Custom made integrated circuitry may be mounted directly onto the patch. This aids the reduction of noise, component count and weight of an fECG monitoring device that may be connected to the patch.

Figure 1:
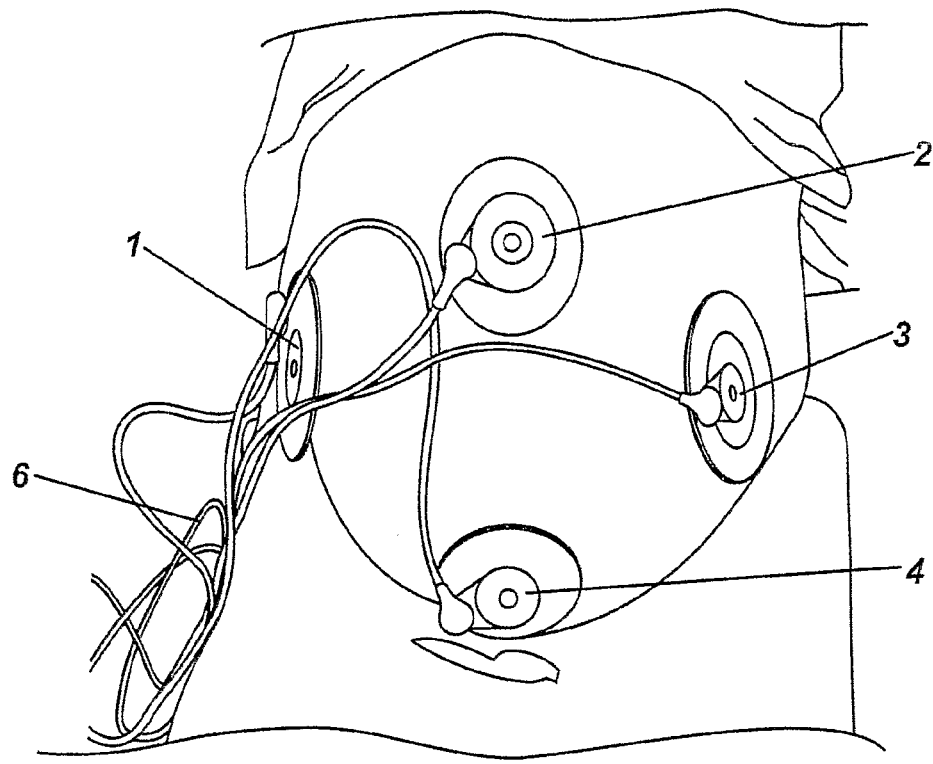
FIG. 1 shows a configuration of discrete electrodes attached to the maternal abdomen of a pregnant subject.

An advantage of deploying an integrated circuit on the patch is the magnitude of reduction in both common and differential mode noise generated by movement artefacts in the associated cables that lead from the monitoring device to the electrodes illustrated in FIG. 1. Single impulse input signals as high as 5 microvolts can be generated, even in a graphite coated anti-triboelectric cable, which can masquerade as phantom fECG signals. In addition to this single shot artefact cable noise there may be repetitive cable noise signals which may be in the order of 0.5 uV-5 uV and may appear as frequencies between 1 Hz-5 Hz. This may create harmonics across the detection bandwidth. These repetitive signals can be created by vibrating the cables or by taut cables resonating e.g. when trapped within a mothers clothing. This may be demonstrated by a cable to a loudspeaker cone and applying a sinusoidal input to the loudspeaker. These rogue electrical signals are generated from both triboelectric effects and inductive coupling with stray EMI and static magnetic sources. Since these noise components are wide bandwidth they conventionally lie unnoticed below the noise floor. It has previously been believed that the noise associated with the interface between the electrodes and the skin was by far the dominant component, and that removing this would solve the issue of SNR in abdominal fECG monitoring. However, due to the additive nature of the squares of each noise component the largest noise will dominate and the cable noise is masked by the electrode-skin noise. For example an electrode noise of 5 uV with a cable noise at 50% (i.e. 2.5 uV) will result in an increase of total noise of only 14% if both noise sources are uncorrelated. Removing (or reducing) the electrode noise reveals the underlying wide bandwidth cable noise and hence by placing the front end amplifier components on the patch reduces the surprisingly large and interfering cable noise.

Mounting the integrated circuitry onto the patch results in a more efficient delivery of the apparatus of a fECG monitoring device. Each channel may comprise an instrumentation amplifier. The common mode rejection ratio of the amplifier may be greater than 100 dB. The input impedance of the amplifier may be greater than 10 MOhms. A signal is fed into the instrumentation amplifier and then into a second amplifier. The integrated circuitry may be configured to provide a total amplification gain of approximately 5000.

The bandwidth of the amplifiers may be set such that it has a lower cut of frequency and an upper cut-off frequency. The selection of the upper and lower cut-off frequencies depends upon the intended use.

In one embodiment the integrated circuitry may for example be configured to have a bandwidth of 76 Hz, the lower cut-off frequency being 4 Hz and the upper cut-off frequency being 80 Hz. This embodiment may for example be used for the detection of fetal heart rate.

In another embodiment the integrated circuitry may for example be configured to have a bandwidth of 249.5 Hz, the lower cut-off frequency being 0.5 Hz and the upper cut-off frequency being 250 Hz. This embodiment may for example be used for morphological applications After a channel is band pass filtered and amplified it is then passed though a multiplexer to an Analogue to Digital Converter. The data is then processed in real time using a digital signal processor using the techniques described in EP1220640/WO01/26545.

Figure 9:
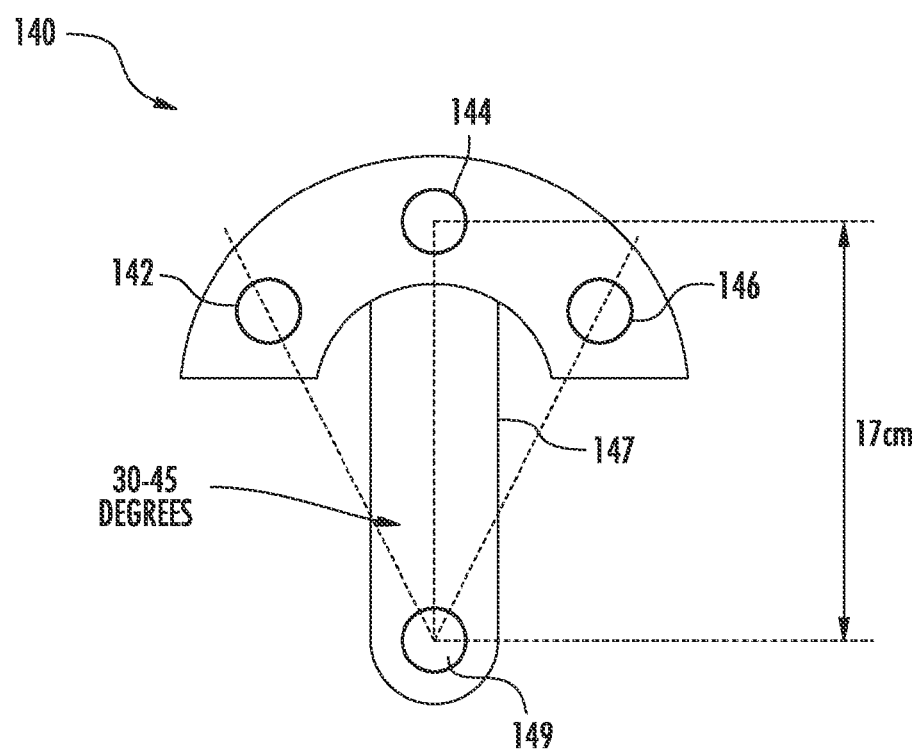
FIG. 9 shows a plan view of an alternative multi-electrode patch.

This invention has addressed at least one or more of the key noise sources (outside of the amplifier voltage and current noise) in abdominal FECG namely:
  Electrode Noise (both white and flicker)—via use of new electrode designs
  Muscle Noise (Electromyogram)—via use of elongated electrodes
  Ambient electromagnetic pick-up noise—via use of a shielded or unshielded flat flexible cable or patch and/or the use of a custom integrated circuit(s) on the patch
  Cable triboelectric/inductive coupling noise—via use of a flat flexible cable or patch With reference to FIG. 9, there is shown an alternative multi-electrode patch 140. This patch may be constructed in the same way as the patch 40 described in connection with FIGS. 5 and 8. However, a difference is in the positioning of a common electrode 149 relative to the sensing electrodes 142, 144 and 146 and placement of the common electrode 149 on the multi-electrode patch.

It has been determined that the electrode locations on an arc which approximates the line of the uterus fundus provide a good success rate for the extraction of fetal heart rate signals. However the success rate is dictated by the signal to noise ratio (SNR) and although the fetal signal heights are relatively large at the uterus fundus it is not necessarily always the optimum location for the best SNR. To identify further optimum positions, a series of midline electrode studies were carried out on the pregnant mother. This consisted of placing a line of 5-6 electrodes from the symphysis pubis vertically to the xiphoid process. The lowest electrode was selected as the common point (corresponding to electrode 149 in FIG. 9) and the resulting fetal signal height and noise was measured at each electrode with respect to the common electrode. A typical set of fetal signal height, noise and SNR results are shown as a function of distance between the electrodes for a 38 week gestational mother in FIGS. 10a, 10b and 10c respectively. The numeric values of distance on the horizontal axes of the graphs represent distance from a common electrode "distance from yellow") 5 cm above the symphysis pubis (SP).

In FIG. 10a we see that the fetal signal height ('FH') is at a maximum at the point of the uterus fundus (UF). However the noise ('NOISE'—FIG. 10b) is also at the maximum at UF and it is increasing at a faster rate than the fetal signal height. The corresponding SNR if (FIG. 10c) shows that at the UF the SNR is a factor of 3. However, if we move back down the midline we see that at 13 cm distance from yellow (i.e. 18 cm from SP) the SNR has now increased to a factor of 6.

FIGS. 10a to 10c represent a single mother and hence we have extended this further by looking at 10 different mothers with again the same midline electrode arrangement for gestational age >37 weeks. FIGS. 11a, 11b and 11c illustrate the corresponding cumulative plots for these 10 different mothers.

We can see that the noise plot follows a similar trend following an approximate square law relationship with respect to the separation of the electrode in question from the common electrode 149. However the rate of increase of the fetal signal height with distance from SP has been modified to a near linear plot. However, dividing the linear plot by the non-linear square law to create the SNR plot for these 10 mothers again shows that the UF is not optimal in terms of SNR. A preferred separation is less than 20 cm (i.e. less than 25 cm from SP) where again here the SNR is a factor of 6. However, if the electrode separation is reduced to less than 10 cm (i.e. less than 15 cm from SP) then although the noise is low and the SNR is still at 6 we notice that the fetal height is less than 5 uV. Such a low magnitude in signal will result in a procedure that is highly vulnerable to noise generated by the electromyogram (EMG) with any slight movement. Hence a compromise is required so that the separation is large enough to be immune from EMG but small enough in order to result in a high SNR. That electrode separation for this gestational period is ~17 cm which is typically 3 cm above the umbilicus. We mention the umbilicus here as the muscle bundles are considerably less around the umbilicus and hence the EMG will be less.

The above results are for late gestation however the gestational weeks 29-32 present significant challenges for fetal ECG detection since this is the vernix period. Vernix is a highly insulating layer that surrounds the fetus and prevents the FECG from being conducted to the surface. Hence SNR's are typically smaller and the optimum separation of the two midline electrodes is even more important. A similar midline study was carried out for the gestational group from 29-32 weeks. FIGS. 12a, 12b and 12c show corresponding results to FIGS. 10a to 10c for a single 30 week gestation period mother. Here, the SNR is 5 at the UF and a maximum of 6 when the separation of the electrodes is 14 cm.

Ten mothers in the vernix period were monitored with a midline study and the aggregated results are shown in FIGS. 13a, 13b and 13c. Again SNR's as high as a factor of 8 can be achieved by placing the electrodes closer together. The optimum electrode separation again depends upon the level of fetal signal height and the danger of it being swamped by the EMG. Initially one could say that this separation is approximately at 12 cm however, we can also see that at 17 cm the SNR is still significant (~5) and this matches with optimum separation for the >37 week gestational group making it highly attractive in terms of ease of delivery to maintain the same separation. However, this results in a position 7 cm above the umbilicus. The fact that the optimum position is not around the umbilicus during the Vernix period is possibly caused by voids in the Vernix being higher up the abdomen.

Further examples are shown in FIGS. 14a, 14b and 14c (35 weeks gestation) and FIGS. 15a, 15b and 15c (24 weeks gestation). Here again setting the separation of the two electrodes at 17 cm presents the best compromise in terms of SNR and EMG rejection. Again as for >37 weeks we can see that the second dashed line (the umbilicus) indicates the optimum position is near this low EMG location of the umbilcus.

In all of these measurements the common electrode 149 has been placed 5 cm above the symphis pubis which provides a physiological reference point on the maternal body. Therefore the optimum position for the central electrode 144 higher up the abdomen is approximately 22 cm above the SP. Preferably, the multi-electrode patch 140 is configured so that the common electrode 149 is on a limb 147 and defines a centre of a circle with the centre sensing electrode 144 and other sensing electrodes 142, 146 lying on a circumference of the circle subtending an arc of approximately 30 to 45 degrees. In another arrangement, the relative positions of sensing electrodes 142, 144 and 146 can be disposed on an arc that approximates the uterus fundus (as shown in FIG. 8) and the common electrode is positioned between 14 and 20 cm below the centre sensing electrode 144.

The advantage of this fixed separation is that a patch 140 is presented that will fit all gestations.

However, it may be desirable to produce two or more sizes of multi-electrode patch which serve different gestation periods. For example, a patch for ≤28 weeks and ≤32 weeks may have a common electrode to sensing electrode separation of 15±2 cm and a patch for 29 to 32 weeks may have a common electrode to sensing electrode separation of 19±2 cm.

More generally, electrodes may be positioned according to the following table:

| gestation period | distance of centre sensing electrode from SP | common electrode to centre sensing electrode separation | distance of centre sensing electrode to umbilicus |
| --- | --- | --- | --- |
| ≤28 weeks | 20 cm ± 2 cm | 15 cm ± 2 cm | 3 cm |
| 29-32 weeks | 23-24 cm | 18-19 cm | 6-7 cm |
| ≥32 weeks | 20 cm ± 2 cm | 15 cm ± 2 cm | 3 cm |

Thus, in a general aspect, the multi-electrode patch may provide a flexible substructure with at least three sensing electrodes positioned on the flexible substructure to approximate an arc, and a common electrode positioned on the flexible substructure, the common electrode being spaced from a centremost one of the sensing electrodes by a distance of between 14 and 20 cm on the concave side of the arc.

Also in a general aspect, the multi-electrode patch may be used for taking fetal ECG measurements by placing the multi-electrode patch on the skin of the pregnant subject such that the common electrode is positioned between approximately 0 and 5 cm above the symphis pubis; placing the sensing electrodes such that a centremost sensing electrode is positioned above the umbilicus; and taking an fECG measurement using any combination of the said at least three sensing electrodes referenced against the common electrode.

Other embodiments are intentionally within the scope of the appended claims.

The invention claimed is:

1. Apparatus for sensing an abdominal fetal electrocardiogram (fECG) signal during any gestational stage of pregnancy, the apparatus comprising:
   a multi-electrode patch comprising:
   a flexible substructure attachable to the skin of a pregnant subject;
   at least three sensing electrodes and a common electrode positioned on the flexible substructure in a predetermined configuration that does not vary with a gestational stage of the pregnant subject, the predetermined configuration including the common electrode defining the center of a circle with said at least three sensing electrodes lying on a circumference of the circle and subtending an arc of approximately 30 to 45 degrees, the common electrode spaced from a centermost one of the sensing electrodes by a distance of between 14 and 20 cm; and
   at least one connection port electrically connected to each sensing electrode and the common electrode; and
   a fetal heart rate monitor electrically connected to the sensing electrodes and the common electrode through said at least one connection port, the fetal heart rate monitor being configured to determine the fECG signal during any gestational stage of pregnancy.

2. Apparatus according to claim 1 wherein the multi-electrode patch further comprises a right leg driver electrode, wherein the flexible substructure includes a spur portion, the right leg driver electrode being located at a distal end of the spur portion.

3. Apparatus according to claim 1, wherein the at least three sensing electrodes include wet gel electrodes.

4. Apparatus according to claim 1, wherein the at least three sensing electrodes include electrodes which each define an electrode contact region greater than 370 square millimeters.

5. Apparatus according to claim 1, wherein the at least three sensing electrodes include electrodes which each define an electrode contact region greater than 490 square millimeters.

6. Apparatus according to claim 1, wherein the at least three sensing electrodes include electrodes which each define a substantially rectangular, elongated or crescent electrode contact region.

7. Apparatus according to claim 1, wherein the at least three sensing electrodes include electrodes which each define a substantially circular electrode contact region.

8. Apparatus according to claim 1, wherein the at least three sensing electrodes are equispaced along the length of the arc.

9. Apparatus according to claim 8 wherein said at least three sensing electrodes include first, second and third electrodes, the spacing of the first electrode from the second electrode being between 80 mm and 100 mm and the spacing of the first electrode from the third electrode being between 80 mm and 100 mm.

10. Apparatus according to claim 8 wherein said at least three sensing electrodes include first, second and third electrodes, the spacing of the first electrode from the second electrode being between 130 mm and 150 mm and the spacing of the first electrode from the third electrode being between 130 mm and 150 mm.

11. Apparatus according to claim 8 wherein said at least three sensing electrodes include first, second and third electrodes, the spacing of the first electrode from the second electrode being between 155 mm and 175 mm and the spacing of the first electrode from the third electrode being between 155 mm and 175 mm.

12. Apparatus according to claim 8 wherein said at least three sensing electrodes include first, second and third electrodes, the spacing of the first electrode from the second electrode being between 230 mm and 250 mm and the spacing of the first electrode from the third electrode being between 230 mm and 250 mm.

13. Apparatus according to claim 8, wherein the multi-electrode patch further includes at least one additional sensing electrode positioned on the line of the arc defined by the at least three sensing electrodes and spaced from a central electrode of the at least three sensing electrodes at a distance different to the spacing from each other of the at least three sensing electrodes.

14. Apparatus according to claim 13 wherein the at least one additional electrode is spaced from the central electrode by a distance of between 80 mm and 100 mm, between 130 mm and 150 mm, between 155 mm and 175 mm or between 230 mm and 250 mm.

15. Apparatus according to claim 1, wherein the at least three sensing electrodes are electrically connected to the connection port by shielded wiring.

16. Apparatus according to claim 15 wherein the flexible substructure and shielded wiring form a flexible flat cable.

17. Apparatus according to claim 1, wherein the flexible substructure includes an adhesive capable of adherence to the skin of the pregnant subject.

18. Apparatus according to claim 1, wherein the multi-electrode patch includes integrated circuitry configured to amplify and filter a detected fetal electrocardiogram signal.

19. A method for taking fetal ECG measurements at any gestational stage of pregnancy, the method comprising the steps of:
a) providing a multi-electrode patch including a flexible substructure attachable to the skin of a pregnant subject, at least three sensing electrodes and a common electrode positioned on the flexible substructure in a predetermined configuration that does not vary with a gestational stage of the pregnant subject, the predetermined configuration including the common electrode defining the center of a circle with said at least three sensing electrodes lying on a circumference of the circle and subtending an arc of approximately 30 to 45 degrees, the common electrode spaced from a centermost one of the sensing electrodes by a distance of between 14 and 20 cm, at least one connection port electrically connected to each sensing electrode and the common electrode;
b) establishing a first line on the skin of the pregnant subject to approximate the line of the uterus fundus;
c) placing the multi-electrode patch on the skin of the pregnant subject such that the at least three sensing electrodes are positioned along a line approximating the first line;
d) placing the common electrode on the skin of the pregnant subject at a location opposing the location of the at least three sensing electrodes such that respective lines taken between the common electrode and each of the sensing electrodes each pass through the womb of the pregnant subject; and
e) taking an fECG measurement using any combination of the said at least three sensing electrodes referenced against the common electrode.

20. A method according to claim 19 wherein step d) includes placing the common electrode at a location approximating the symphysis pubis of the pregnant subject.

21. A method according to claim 19 including, after step d), the sub-step of:
placing a right leg driver electrode on the back or abdominal side of the pregnant subject.

22. A method according to claim 19 wherein the electrodes arranged on the multi-electrode patch each define a substantially circular electrode contact area.

23. A method according to claim 19, further including the steps of:
placing a further electrode on the back or abdominal side of the pregnant subject;
connecting the further electrode to the heart rate monitor; and
driving a signal back into the pregnant subject to cancel out signals common to each of the sensing electrodes and wires connecting to the sensing electrodes.

24. A method for taking fetal ECG measurements at any gestational stage of pregnancy, the method comprising the steps of:
a) providing a multi-electrode patch for use on a pregnant subject regardless of the gestational stage of pregnancy of the pregnant subject, the patch having:
a flexible substructure attachable to the skin of a pregnant subject;
at least three sensing electrodes and a common electrode positioned on the flexible substructure, the common electrode defining the center of a circle with said at least three sensing electrodes lying on a circumference of the circle and subtending an arc of approximately 30 to 45 degrees, the common electrode spaced from a centermost one of the sensing electrodes by a distance of between 14 and 20 cm, a predetermined position of the sensing electrodes and the common electrode relative to each other not varying as a function of the gestational stage of pregnancy, at least one connection port electrically connected to each sensing electrode and the common electrode and electrically connected to a fetal heart rate monitor;
b) placing the multi-electrode patch on the skin of the pregnant subject at any gestational stage of pregnancy such that the common electrode is positioned between approximately 0 and 5 cm above the symphysis pubis;
c) placing the sensing electrodes such that the centremost sensing electrode is positioned above the umbilicus; and
d) taking an fECG measurement using any combination of the said at least three sensing electrodes referenced against the common electrode.

25. A method for taking fetal ECG measurements comprising the steps of:
providing a multi-electrode patch including a flexible substructure attachable to the skin of a pregnant subject, at least three sensing electrodes and a common electrode positioned on the flexible substructure, each sensing electrode defining a substantially rectangular, elongate or crescent electrode contact area and having a respective longitudinal axis, each sensing electrode being spaced apart from the other sensing electrodes and from the common electrode;
placing the multi-electrode patch on the skin of the pregnant subject such that the at least three sensing electrodes are positioned such that the longitudinal axis of the contact area of each sensing electrode is transverse to a respective underlying abdominal muscle of the pregnant subject;

connecting each of the electrodes to a fetal heart rate monitor; and taking an fECG measurement using any combination of said at least three sensing electrodes referenced against the common electrode.

* * * * *

UNITED STATES PATENT AND TRADEMARK OFFICE
CERTIFICATE OF CORRECTION

| | | |
|---|---|---|
| PATENT NO. | : 8,880,140 B2 | Page 1 of 1 |
| APPLICATION NO. | : 12/997566 | |
| DATED | : November 4, 2014 | |
| INVENTOR(S) | : Barrie Robert Hayes-Gill et al. | |

It is certified that error appears in the above-identified patent and that said Letters Patent is hereby corrected as shown below:

On the Title Page:
Item (73), Assignee: delete "Minoca Healthcare Limited" and replace with --Monica Healthcare Limited--

Signed and Sealed this
Twenty-fourth Day of February, 2015

Michelle K. Lee
*Deputy Director of the United States Patent and Trademark Office*